(12) United States Patent
Szogi et al.

(10) Patent No.: US 8,906,332 B2
(45) Date of Patent: Dec. 9, 2014

(54) GASEOUS AMMONIA REMOVAL SYSTEM

(75) Inventors: Ariel A. Szogi, Florence, SC (US);
Matias B. Vanotti, Florence, SC (US);
Michael J. Rothrock, Bangor, ME (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 687 days.

(21) Appl. No.: 13/048,375

(22) Filed: Mar. 15, 2011

(65) Prior Publication Data
US 2011/0229403 A1    Sep. 22, 2011

Related U.S. Application Data

(60) Provisional application No. 61/314,683, filed on Mar. 17, 2010.

(51) Int. Cl.
| | | |
|---|---|---|
| *B01D 53/34* | (2006.01) |
| *C01C 1/242* | (2006.01) |
| *B01D 53/22* | (2006.01) |
| *C07C 51/41* | (2006.01) |
| *C01C 1/16* | (2006.01) |
| *C01C 1/28* | (2006.01) |
| *C01C 1/18* | (2006.01) |

(52) U.S. Cl.
CPC ............ *B01D 53/22* (2013.01); *B01D 2251/50* (2013.01); *C01C 1/242* (2013.01); *B01D 2258/06* (2013.01); *B01D 2258/0266* (2013.01); *B01D 2257/406* (2013.01); *C07C 51/412* (2013.01); *C01C 1/164* (2013.01); *C01C 1/28* (2013.01); *B01D 2251/70* (2013.01); *C01C 1/185* (2013.01)
USPC .......................................... 423/237; 423/549

(58) Field of Classification Search
USPC ................. 423/549, 235, 237, 238, 239.1
See application file for complete search history.

(56) References Cited

U.S. PATENT DOCUMENTS 7,674,379 B2 *   3/2010   Vanotti et al. ................. 210/605

\* cited by examiner

*Primary Examiner* — Edward Johnson
(74) *Attorney, Agent, or Firm* — Gail E. Poulos; John Fado; Lesley Shaw

(57) ABSTRACT

A system and method for passive capture of ammonia in an enclosure containing material that gives off ammonia. The invention allows for the passage of gaseous $NH_3$ through microporous hydrophobic gas-permeable membranes and its capture in a circulated acidic solution with concomitant production of a concentrated non-volatile ammonium salt.

13 Claims, 15 Drawing Sheets

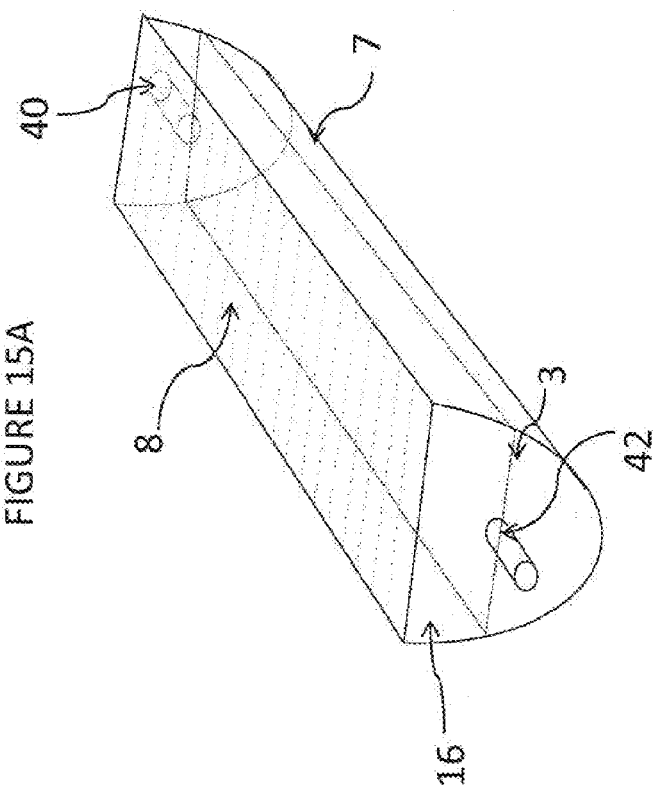
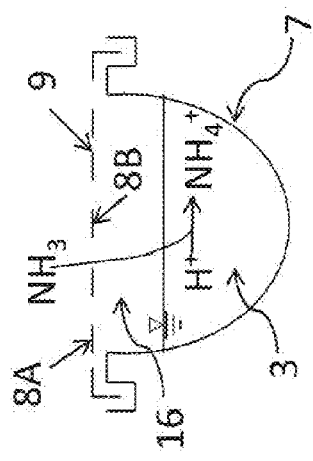
FIGURE 15A
FIGURE 15B

GASEOUS AMMONIA REMOVAL SYSTEM

This application claims priority to U.S. Provisional Patent Application Ser. No. 61/314,683, filed Mar. 17, 2010, the contents of which are incorporated herein by reference in their entirety.

FIELD OF THE INVENTION

This invention relates to a system and method for the removal of gaseous nitrogen and its conversion to non-volatile nitrogen-containing compounds to reduce emissions from systems that produce gaseous nitrogen.

BACKGROUND OF THE ART

One of the largest environmental concerns associated with raising poultry for production in confined enclosures is the accumulation of ammonia gas ($NH_3$). Volatilization of $NH_3$ inside poultry housing often results in an excessive accumulation of $NH_3$ in the air, which can negatively affect the health of both workers and birds (Kirychuk et al., Journal of Occupational and Environmental Medicine 48 (7):741-748, 2006; Ritz et al., Journal of Applied Poultry Research 13:684-692, 2004; Rylander and Carvalheiro, International Archives of Occupational and Environmental Health 79 (6):487-490) 2006).

Numerous studies have shown the detrimental effect of high levels of $NH_3$ on bird productivity (Dawkins et al., Nature 427 (6972):342-344, 2004; Ritz et al., supra; Wathes et al., Transactions of the American Society of Agricultural Engineers 45 (5):1605-1610, 2002; Yahav, Animal Research 53:289-293, 2004). Although increased ventilation can lower the $NH_3$ in poultry houses to safe levels, it is expensive due to energy costs during winter months (Moore et al., 1995, Journal of Environmental Quality, Volume 24, 293-300). Since $NH_3$ cannot be effectively contained within the house structure, $NH_3$ emissions may contribute to air pollution, atmospheric deposition, and health concerns for near-by residents (Nahm, 2003, World's Poultry Science Journal, Volume 59, 77-88; Wheeler et al., 2006, Transactions of the American Society of Agricultural Engineers, Volume 49(5), 1495-1512; Williams et al., 1999, Reviews of Environmental Contamination and Toxicology, Volume 162, 105-157; Wing and Wolf, 2000, Environmental Health Perspectives, Volume 108(3), 233-238).

Ammonia levels as low as 20 ppm have been found to compromise the immune and respiratory systems of chickens, making them more susceptible to disease. High levels of ammonia also negatively affect their feed conversion and weight gain. As a result of all these negative impacts on performance, recommended ammonia concentrations in poultry barns should be well below 25 ppm.

High levels of ammonia may also pose a risk to the health of agricultural workers in chicken rearing facilities; exposure to ammonia can irritate the respiratory tract and eyes, even at low levels. Therefore, the Federal Occupational Safety and Health Administration (OSHA) permissible worker exposure limit for ammonia is 50 ppm over an 8-hour period and the American Conference of Governmental Industrial Hygienists (ACGIH) has established a short-term (15-min) exposure limit of 35 ppm.

Current $NH_3$ abatement technologies used in livestock houses rely on the ventilation systems and treatment of the exhaust air after leaving the house to remove nitrogen. Typically such systems are large requiring a lot of power that allows for an exchange range from 275 to 451 cubic feet of air per second depending on ambient temperatures (colder and warmer, respectively), assuming an average weight per broiler of 1.3 kg and 20000 broilers per house (American Society of Agricultural and Biological Engineers, Design of Ventilation Systems for Poultry and Livestock Shelters, ASABE Standard Practices, ASAE EP270.5 December 1986 (R2008), 1986). Such massive ventilation allows for the dilution of indoor ammonia levels and it does increase the removal amounts of ammonia from poultry facilities. However, ammonia releases from such facilities in this manner to the atmosphere is expensive in the colder months and throughout the year can cause environmental problems, such as acid precipitation, fine particulate matter formation (particulate matter with an aerodynamic diameter less than ten microns in size), and nitrogen deposition into aquatic systems. The accumulated effects of ventilation contribute to a reduction in the quality of life and raise health concerns for near-by residents.

A second strategy includes treating the $NH_3$ in the exhaust air from enclosures using scrubbing or filtration techniques, thus preventing $NH_3$ release into the environment. This technique consists of forcing the ventilated air through an $NH_3$ trap, such as an acidic solution (scrubbers), or through a porous filter with nitrifying biofilms that oxidize $NH_3$ to nitrate (biotrickling or organic filters) (Chen et al., Chemosphere 58 (8):1023-1030, 2005; Melse and Ogink, Transactions of the ASAE 48 (6):2303-2313, 2005; Ndegwa et al., Biosystems Engineering 100:453-469, 2008; Pagans et al., Chemical Engineering Journal 113 (2-3):105-110, 2005). The process is costly in winter months when it is necessary to heat enclosures to maintain production. In addition, recent research has shown that $NH_3$ concentrations close to the litter surface (<20 cm), where the birds are exposed, can be up to one order of magnitude higher than in the bulk house air.

The third technology is to selectively pull and treat the air near the litter surface, where $NH_3$ levels are more concentrated, using dedicated ventilation systems independent of the house ventilation system (Lahav et al., Water Air Soil Pollution, Volume 191, 183-197, 2008). A significant departure from the methods described above is the concept of removing $NH_3$ using manifolds that extract only the air close to the litter independent of the house ventilation system. These systems require redundancy, additional positive air extraction equipment and are thus not cost effective.

A fourth form of abatement is to add chemical amendments directly to the poultry litter to prevent $NH_3$ volatization, without the need of additional ventilation to move $NH_3$. These amendments act by either inhibiting microbial transformation of urea or uric acid into $NH_3$ or by acidifying and neutralizing it. Several chemical amendments have been widely used for their ability to control or reduce $NH_3$ release from poultry litter and manure, such as $AL_2(SO_4)_3 \cdot 14H_2O$ (Al+Clear®), $NaHSO_4$ (PLT®), and acidified clays (Poultry Guard®) (Cook et al., Journal of Environmental Quality 37:2360-2367, 2008; Moore et al., 1995, supra; Moore et al., Journal of Environmental Quality 29:37-49, 2000; Shah et al., Poultry litter amendments, edited by N. C. C. E. Service. Raleigh, N.C.: North Carolina State University, 2006). Although N is conserved unvolatilized in the poultry litter, $NH_3$ is not recovered as a separate product as with the scrubbing techniques. Recovery of $NH_3$ is a desirable feature because it can be exported off the farm, solving problems of N surpluses in concentrated poultry production regions.

Conservation and recovery of nitrogen (N) is also important in agriculture because of the high cost of producing and acquiring commercial $NH_3$ fertilizers. Thus, there is a desire to improve technologies for abating $NH_3$ emissions from confined poultry operations by capturing and recovering nitrogen.

While, various systems have been developed for removing $NH_3$ from animal litter, there still remains a need in the art for different abatement systems that removes $NH_3$ from gaseous nitrogen producing systems and recovers the N in a concentrated purified form, but is not dependent on intense air movement. The present invention, different from prior art systems, provides such systems using hydrophobic gas-permeable membranes and circulated acidic solutions to produce concentrated ammonium salt.

SUMMARY OF THE INVENTION

It is therefore ah object of the present invention to provide a system for at least reducing levels of $NH_3$ in an enclosed area and recovering N in a purified concentrated form.

Another object of the present invention is to at least reduce the level of $NH_3$ in an enclosure using systems that do not require large capacity airflow handling systems.

A still further object of the present invention is to provide a system for at least reducing the levels of $NH_3$ in an enclosed space using systems that capture $NH_3$ in a circulated acidic solution with the concomitant production of a concentrated ammonium salt.

A still further object of the present invention is to provide a system for at least reducing the levels of $NH_3$ in an enclosed area using systems that remove $NH_3$ through the use of microporous, hydrophobic, gas-permeable membranes.

Another object of the present invention is to provide a system for at least reducing the levels of $NH_3$ in an enclosed area using systems that remove $NH_3$ through the use of microporous, hydrophobic gas-permeable membranes and chemical amendment of animal litter used in the enclosed space.

A still further object of the present invention is to provide a system for at least reducing the levels of $NH_3$ in an enclosed space containing animal litter wherein in said litter includes a chemical which enhances $NH_3$ release from the litter.

Another object of the present invention is to provide a system for at least reducing the levels of $NH_3$ in a composting system and recovering N in a purified concentrated form.

Another object of the present invention is to provide a method for at least reducing $NH_3$ in an enclosed space using a system that does not require large capacity airflow handling systems.

A still further object of the present invention is to provide a method for at least reducing $NH_3$ in ah enclosed space using a system that captures $NH_3$ in a circulated acidic solution with the concomitant production of a concentrated ammonium salt.

A still further object of the present invention is to provide a method for at least reducing $NH_3$ in an enclosed space using a system having microporous, hydrophobic, gas-permeable membranes.

Another object of the present invention is a method for at least reducing $NH_3$ in an enclosed space using a system having microporous, hydrophobic gas-permeable membranes and a chemical amendment of an animal litter used in the enclosed space wherein said amendment increases the release of $NH_3$ from the litter.

A still further object of the present invention is to provide a method for at least reducing $NH_3$ in a composting system using a system having microporous, hydrophobic gas-permeable membranes.

Further objects and advantages of the invention will become apparent from the following description.

was run for the acidic solution (without poultry litter). All points represent mean values of duplicate numbers.

FIG. 9A is a graph showing the mass of $NH_3$ recovered in the acidic solution and FIG. 9B is a graph showing $NH_4$—N remaining in the poultry litter (PL) from chambers amended with hydrated lime ($Ca(OH)_2$). Day 1 litter values in FIG. 9B represent initial samples that remained on the bench-top for one day prior to analysis to determine the rapid release of $NH_3$ from the litter. The controls (▼) were run for both the acidic solution and poultry litter as described. All points represent the mean of duplicate chambers, and the error bar in the upper right hand corner of the graphs represents the $LSD_{0.05}$ value for the $NH_3$ recovered in the acidic solution (approximately 50.711) and $NH_4$—N remaining in the litter (approximately 123.19).

Figure 10:
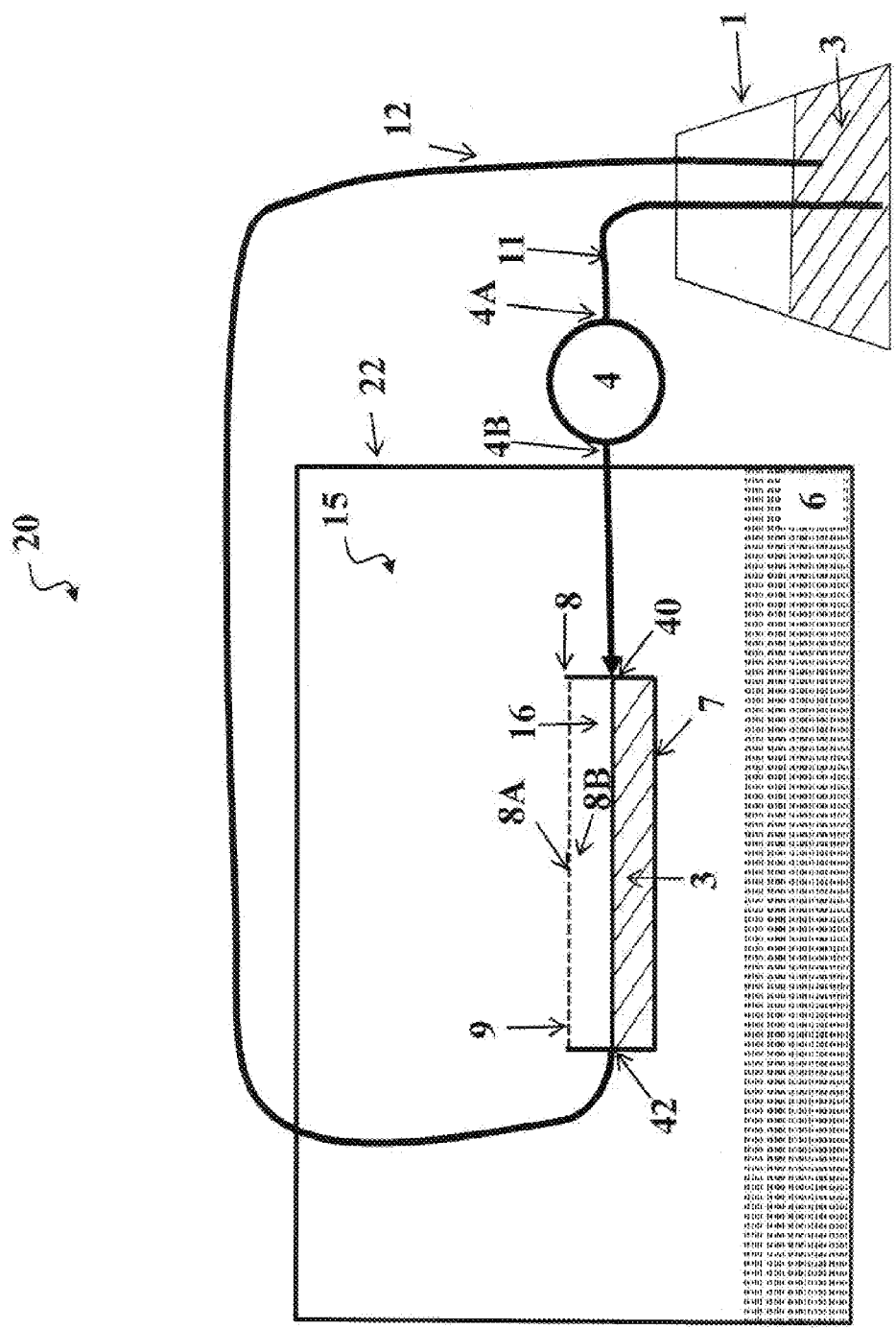

FIG. 10 is a cross section schematic diagram of ammonia ($NH_3$) capture system 20 using hydrophobic gas-permeable flat membrane. Shown in the diagram are acid solution ($NH_3$ sink) 3, acid tank 1 for acid solution, intake flow line 11, pump discharge flow line 12, fluid pump 4, pump intake end 4A, pump discharge end 4B, and enclosure or barn 22, $NH_3$ emitting source (Poultry Litter, for example) 6, membrane assembly 15 including trough covered with flat membrane 7 exposed to air with $NH_3$ hydrophobic, gas-permeable flat membrane outer surface 8A, membrane pores 9, acid solution 3 flowing within trough 7, and membrane air space 16 between membrane inner surface 8B and surface of acid solution 3 flowing within trough 7, membrane assembly entry opening 40 and membrane assembly exit opening 42.

Figure 11:
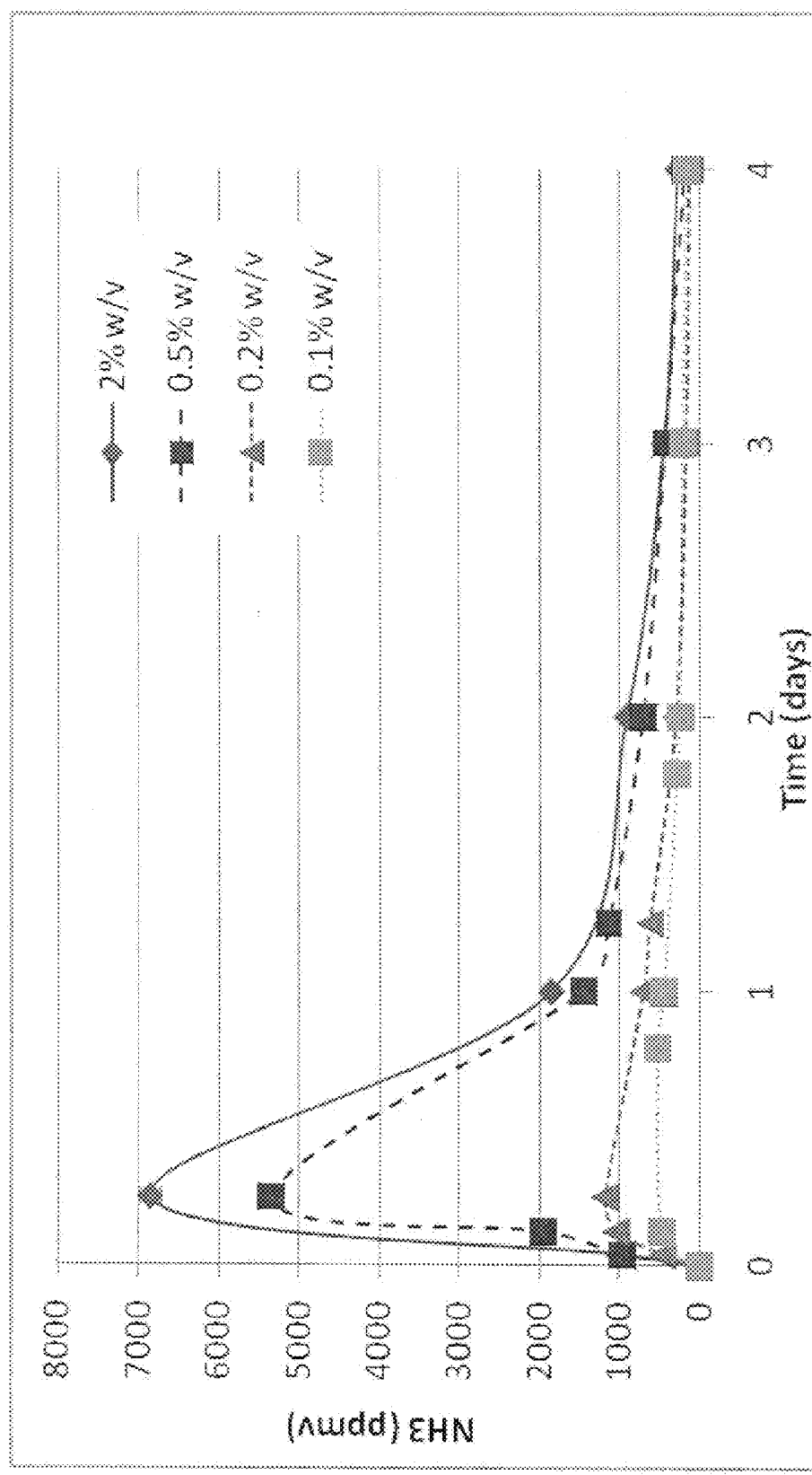

FIG. 11 is a graph showing rapid reduction of gaseous ammonia from air within enclosures using a flat membrane prototype with poultry litter. Various concentrations of $NH_3$ in the air (approximately 0 to 6 hours) were established using different rates of hydrated lime ($Ca(HO)_2$) applied to the emitting source (poultry litter) at time=0.

Figure 12:
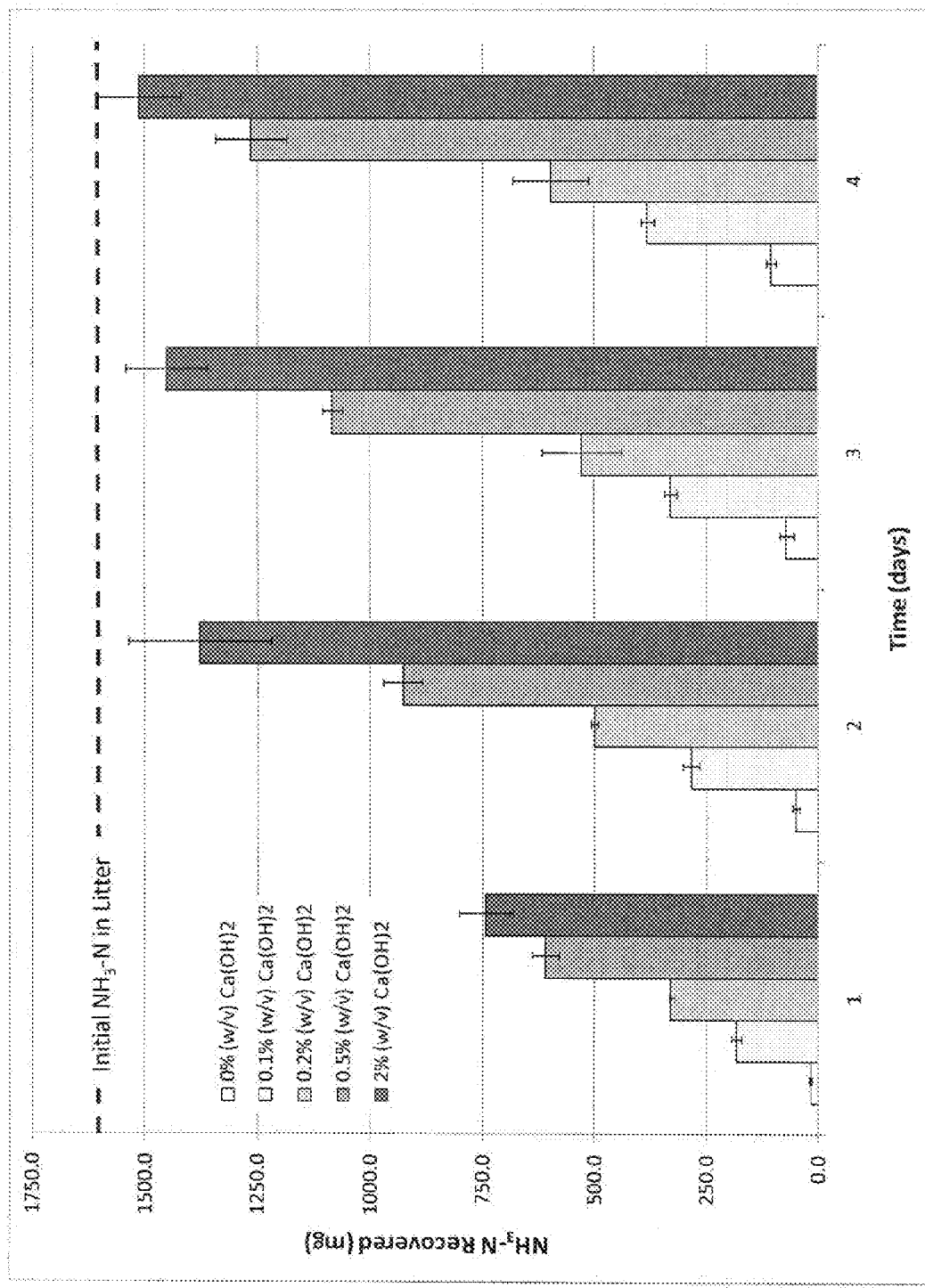

FIG. 12 is a graph showing recovery of ammonia from poultry litter using a flat membrane prototype. The litter was treated with different rates of hydrated lime ($Ca(HO)_2$) to increase the concentration of $NH_3$ in the air. The dashed horizontal line represents the mass of $NH_4$—N initially present within the poultry litter. Error bars represent the standard deviation of duplicate experiments.

Figure 13:
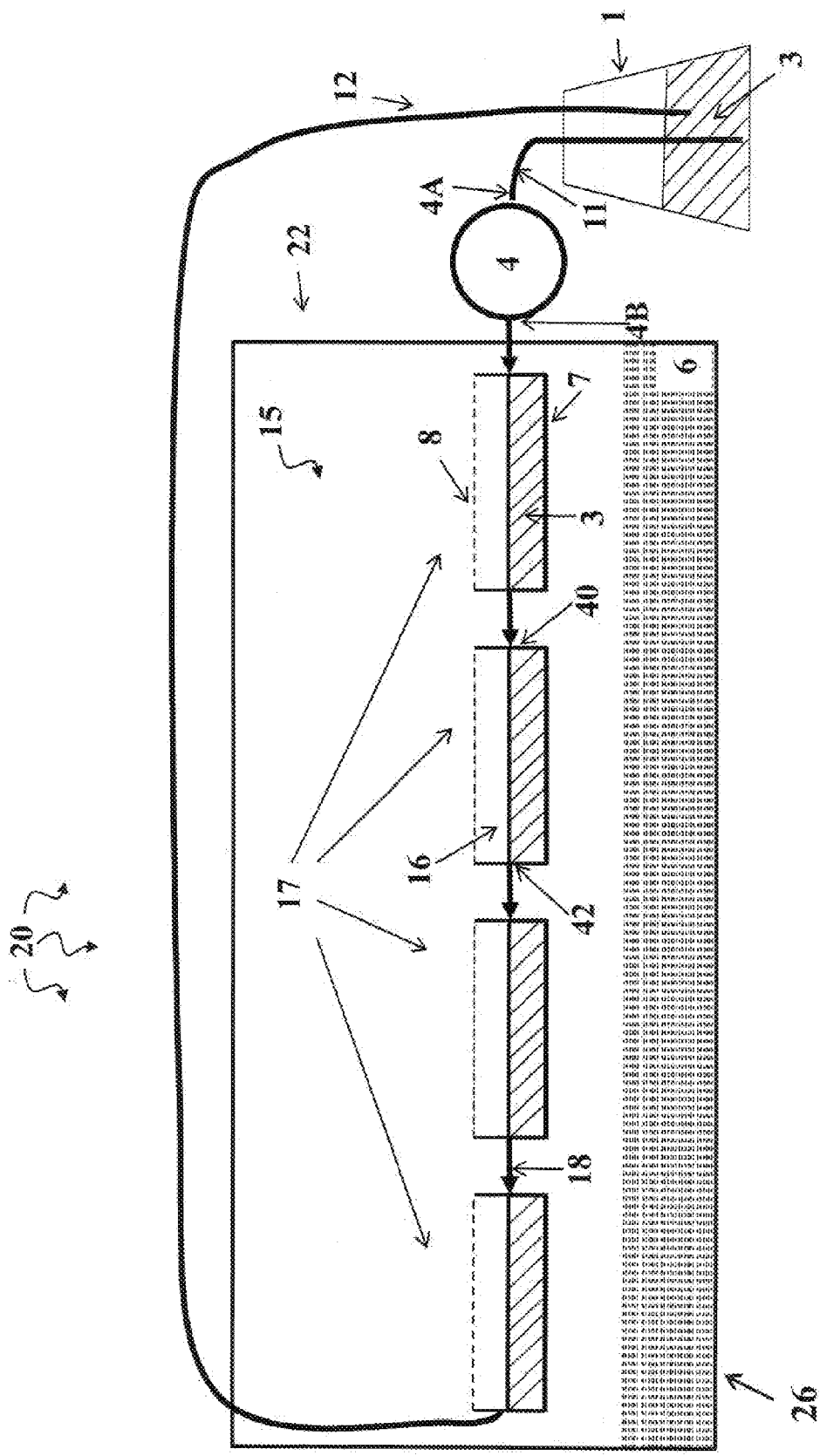

FIG. 13 is a cross section schematic diagram of ammonia ($NH_3$) capture system 20 from poultry litter using a membrane system 15 having a hydrophobic gas-permeable flat, membrane manifold system 17 including multiple troughs 7 connected in series. Shown in the diagram are acid solution ($NH_3$ sink) 3 Acid tank/reservoir 1 for acid solution, intake flow line 11, discharge flow line 12, fluid, pump 4 with intake end 4A and discharge end 4B, enclosure or barn 22, $NH_3$ emitting source (Poultry Litter, for example) 6, trough 7 covered with flat membrane 8 exposed to air with $NH_3$ hydrophobic, gas-permeable membrane 8 in flat configuration, acid solution 3 flowing within trough 7, and membrane air space 16 between inner membrane surface and surface of acid solution 3 flowing within trough 7. Also shown are membrane assembly entry opening 40 and membrane assembly exit opening 42, acid flow pipe 18.

Figure 14:
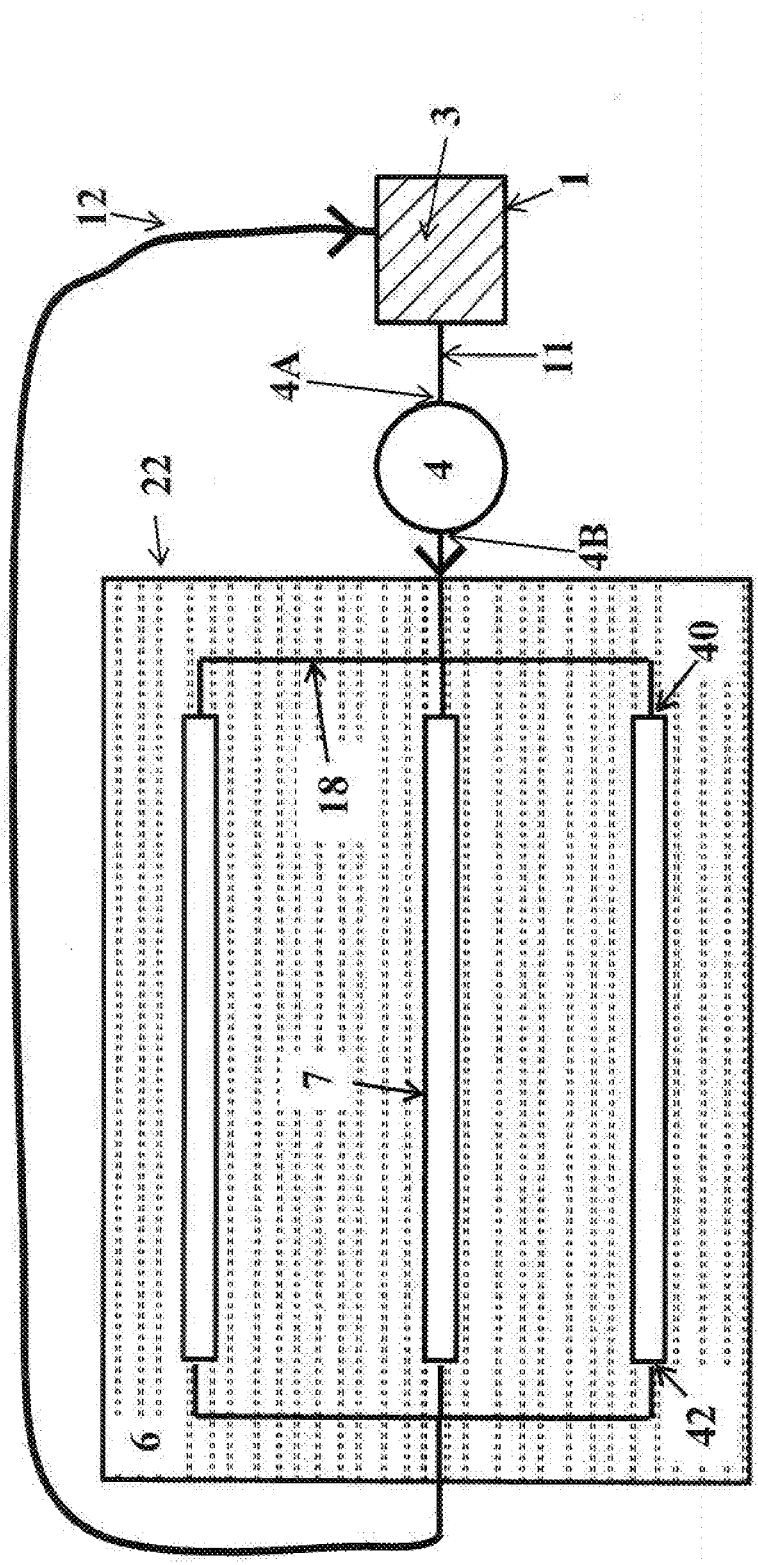

FIG. 14 is an aerial view schematic diagram of ammonia ($NH_3$) capture system from using multiple hydrophobic gas-permeable flat membrane troughs 7 connected in parallel. Shown in the diagram are acid solution ($NH_3$ sink) 3, acid tank 1 for acid solution, intake flow line 11, discharge flow line 12, fluid pump 4 with intake end 4A and discharge end 4B, enclosure or barn 22, $NH_3$ emitting source 6, hydrophobic gas-permeable flat membrane troughs 7, acid flow pipes 18, and membrane assembly entry opening 40 and membrane assembly exit opening 42.

FIG. 15A is a three dimensional schematic diagram of plastic trough 7 with flat gas permeable membrane 8 to remove $NH_3$ from the air acid solution 3, membrane assembly entry opening 40 and membrane assembly exit opening 42, and 15B is a cross section schematic diagram of the same trough with flat gas permeable membrane outer surface 8A, membrane pore 9, and membrane air space 16 between inner membrane surface 8B and surface of the acid solution 3.

DETAILED DESCRIPTION

Figure 1:
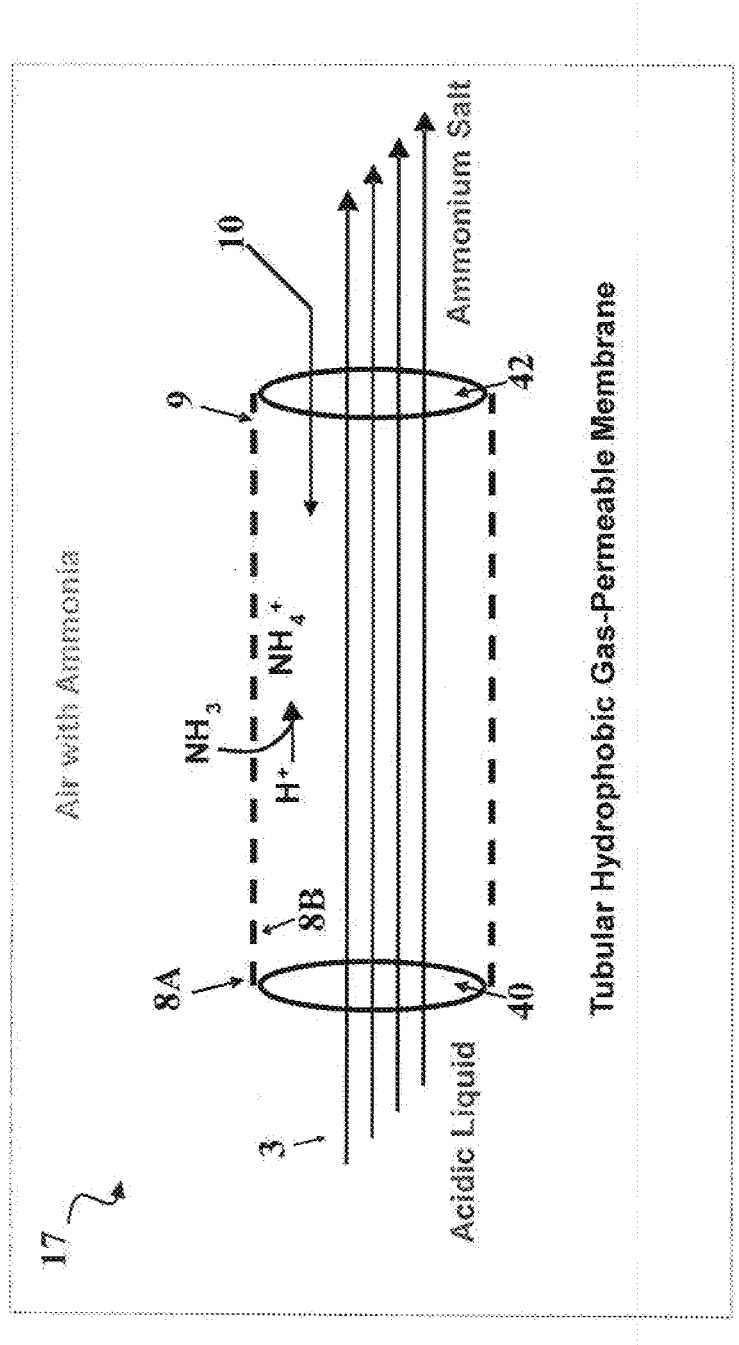
FIG. 1 is a cross-sectional drawing of ammonia capture using hydrophobic gas-permeable tubing 8 and shows membrane manifold system 17 including membrane 8, membrane outer surface 8A, membrane inner surface 8B, membrane pores 9, hollow interior of tubular membrane 10, membrane assembly entry opening 40 and membrane assembly exit 42. Ammonia gas ($NH_3$) permeates through hydrophobic membrane 8 walls with micron-sized pores 9, where it combines with the free protons ($H^+$) in the acid solution 3 to form non-volatile ammonium ions ($NH_4^+$).

The present invention recovers N in a concentrated purified form, but is not dependent on intense air movement. The invention is an ammonia gas capture system 20 that includes the passage of $NH_3$ through a membrane assembly 15 that includes at least one microporous hydrophobic gas-permeable membrane 8 and the capture of $NH_3$ in a circulated acid solution 3 with concomitant production of a concentrated-ammonium salt. Once $NH_3$ is in contact with the acid solution 3 it reacts with free protons ($H^+$) to form non-volatile ammonium ($NH_4^+$) salt, which is retained and concentrated in the acid solution 3 (FIGS. 1 and 10).

Modern animal production is an extremely sophisticated business and the management, treatment, purification, and appreciation of its by-products should also be so. As the practice of intensive production in enclosed areas, such as for example, stables, barns, poultry houses, pen facilities, etc., grows there is an increasingly urgent need for effective and affordable alternatives for management of nutrient by-products.

Figure 2:
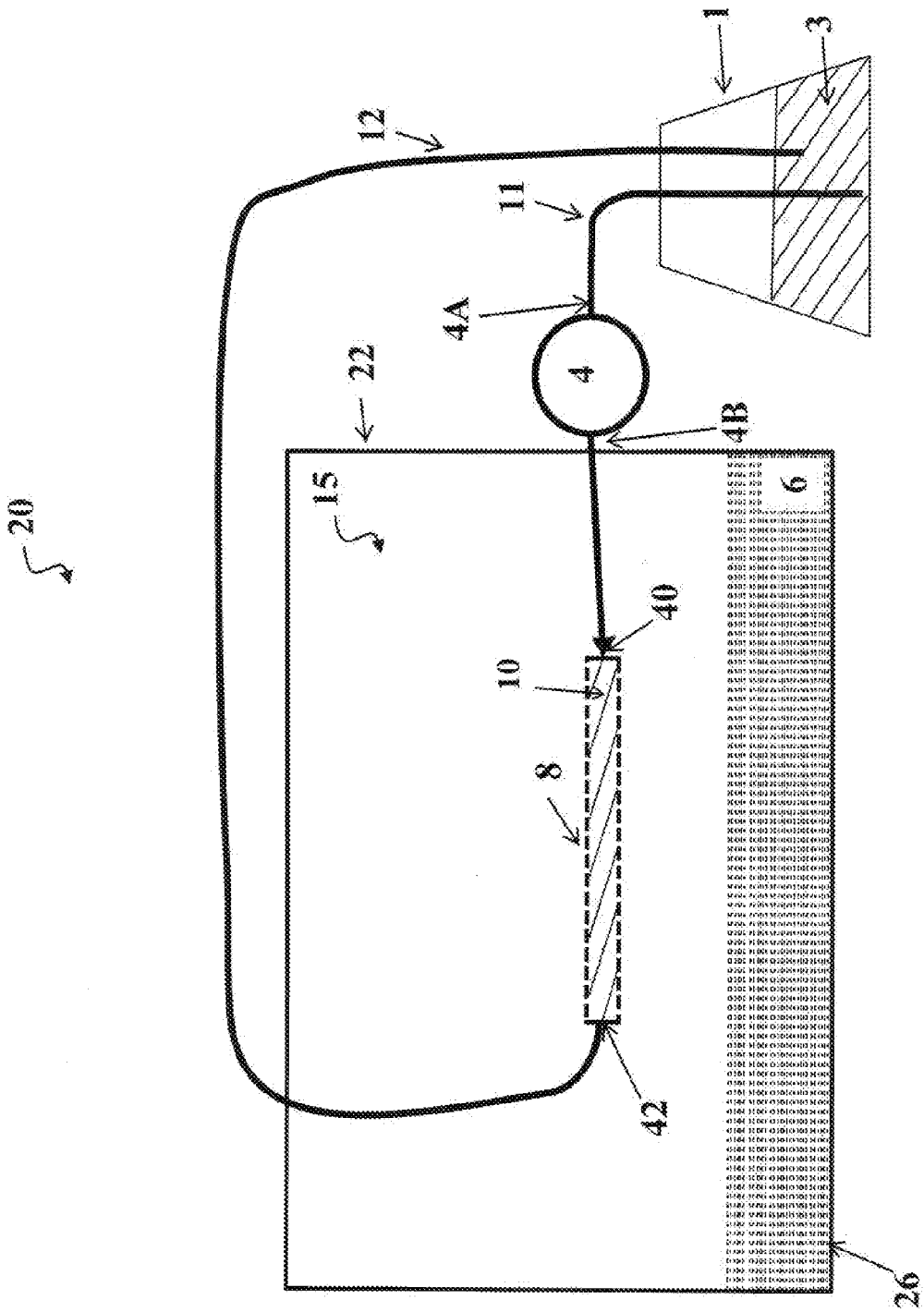
FIG. 2 is a diagram showing a basic configuration of system 20 for $NH_3$ recovery showing membrane system or assembly 15 having acid tank 1, acid solution 3, fluid pump 4, hydrophobic, microporous, gas permeable membrane 8 in a tubular configuration, pump intake flow line 11 and pump discharge flow line 12, a first membrane assembly entry opening 40 and a membrane assembly exit opening 42, and further showing enclosure/chamber 22, and $NH_3$, emitting source 6.

The removal and recovery of $NH_3$ is a desirable feature because it can be exported off the farm which solves the problems of nitrogen surpluses in concentrated farm animal production regions. The present invention uses gas-permeable membranes that are placed inside an enclosure housing farm animals for production to recover nitrogen in a concentrated purified form and is not dependent on intense airflow. According to ASABE standards, required Ventilation ranges from 275 to 451 cubic feet of air per second depending on ambient temperatures (colder and warmer, respectively), assuming an average weight per broiler of 1.3 kg and 20,000 broilers per house (American Society of Agricultural and Biological Engineers, Design of Ventilation Systems for Poultry and Livestock Shelters, ASABE Standard Practices, ASAE EP270.5 December 1986 (R2008), 1986). As shown in FIGS. 1, 2, and 10, the invention allows for the passage of gaseous $NH_3$ through microporous hydrophobic gas-permeable membranes 8 and its capture in a circulated acid solution 3 with concomitant production of a concentrated non-volatile ammonium salt. Once the $NH_3$ is in contact with the acid solution 3, it reacts with free protons ($H^+$) to form the non-volatile ammonium ($NH_4^+$) salt, which is retained and concentrated in the acid solution 3.

Hydrophobic, gas-permeable membrane 8 includes, for example, polypropylene (Shindo et al., Gas transfer process with hollow fiber membrane. Japan: Mitsubishi Rayon, Co., Ltd., 1981), polyethylene/polyurethane composites (Lee and Rittmann, Water Science Technology 41:219-226; 2000), or polytetrafluoroethylene (PTFE) (Blet et al, Analytica Chimica Acta, Volume 219, 309-311, 1989). Membrane 8 can be tubular or flat as shown in FIGS. 2 and 10. Semi permeable membrane 8 includes but is not limited to hydrophobic gas permeable hollow fiber membranes 8 (FIGS. 1 and 2) made from polypropylene (Shindo et al., Gas transfer process with hollow fiber membrane. Japan: Mitsubishi Rayon, Co., Ltd., 1981), and polyethylene/polyurethane composites (Lee and Rittmann, 2000, supra), silicone rubber (Carlson, R. M. 1978. Automated Separation and Conductometric Determination of Ammonia and Dissolved Organic Carbon. Anal. Chem. 50: 1528-1531), polysulfone, polytetrafluoroethylene (PTFE) (Blet et al., supra) or expanded polytetrafluoroethylene (ePTFE). See also U.S. Pat. No. 5,474,660 and No. 5,071,561 herein incorporated in their entirety by reference.

FIGS. 2 and 10 are schematic diagrams showing the interior of an enclosure 22 and the ammonia capture system 20 of the invention, $NH_3$ emitting source (poultry litter, for example) 6 is soiled with waste products that primarily include urine and feces and possibly undigested nitrogen-containing feed. The nitrogen present in these waste materials is located on the floor 26 of enclosure 22 and ammonia gas generated from said urine, feces and/or food permeates the enclosure. A membrane assembly 15 includes a microporous, hydrophobic, gas-permeable membrane 8 that is disposed within enclosure 22 and is in closed-loop communication via fluid pump 4 with an acid solution 3 contained in reservoir 1. Membrane 8 includes an outer surface 8A, and inner surface 8B, membrane pores 9, and membrane assembly entry opening 40 and a membrane assembly exit opening 42.

For purposes of the present invention the term litter is defined as any material put on the bottom surface of an enclosed space that can be bedding for an animal, for example and/or contains waste products including urine, feces and possibly undigested nitrogen-containing feed.

For purposes of the present invention, the term enclosure is defined as any structure having an area that has been enclosed such as for example, stables, barns, poultry houses, animal pens, composting bins, anaerobic disgesters, etc.

Furthermore, for purposes of the present invention, ammonia capture system 20 can be used to capture ammonia from composting. For purposes of the present invention, the term composting is defined as any bioxidative process involving the mineralization and partial humification of organic matter leading to stabilized usable substances called compost. During the composting process the simple organic compounds are mineralized and metabolized by the microorganisms producing $CO_2$, $NH_3$, $H_2O$, organic acids, and heat The membrane assembly 15 including membrane 8 functions as a passive getter for ammonia gas and as the gas is captured, production of more gas from non-volatile $NH_4$ occurs until all or substantially all of the $NH_4$ is converted to $NH_3$.

The membrane 8 itself is a tubular or flat microporous, hydrophobic, gas-permeable membrane 8 having membrane pores 9. The tubular membrane 8 is defined as an endless circumferential material having an outer surface 8A and an inner surface 8B (see FIG. 1). The inner surface 8B defines a hollow interior 10 (FIG. 1). Thus the permeable membrane 8 allows for the diffusion of ammonia gas concentrated outside the outer surface 8A to diffuse through the membrane 8 to the hollow interior 10. Another embodiment of membrane 8 is the use of a flat, microporous, hydrophobic, gas-permeable membrane (FIG. 10) such as, for example, PTFE, ePTFE, polypropylene, polypropylene-backed ePTFE laminates, nylon-backed ePTFE laminates, and polyethylene-backed ePTFE laminates. Membrane 8 is defined by an upper and a lower surface, each having an outer 8A and inner 8B surface. The flat membrane is stretched over a trough 7 which contains flowing acid solution 3 with an air space 16 between membrane 8 and acid solution 3. It operates by allowing for the diffusion of ammonia gas concentrated outside the outer surface 8A to diffuse through membrane 8 to the interior into membrane air space 16.

Hollow, tubular, gas-permeable membranes typically have wall thickness ranging from 0.1-2.0 mm, inner diameter ranging from 0.3-100 mm, bubble point ranging from 3–300 kPa, and porosity ranging from 40-80%. The tubular membranes can be assembled in modules with several tubings parallel to each other and a common intake and outtake. Flat, gas-permeable membranes are typically defined by their membrane thickness (ranging from 0.001-0.2 mm), bubble point (ranging from 3–300 kPa), and porosity (ranging from 40-80%). Flat membrane surface area was equivalent to approximately 11 to 14% of the enclosure surface area in both the bench-scale and field-scale experiments.

The closed loop delivery system for delivering acid from acid tank/reservoir 1, in FIGS. 2 and 10, to the hollow interior 10 of tubular membrane 8 or to membrane airspace 16 in trough 7 of membrane assembly 15 including flat membrane 8 is composed of fluid pump 4 having an intake end 4A and discharge end 4B and at least two hollow flow lines 11 and 12 having distal and proximal ends. Discharge flow line 12 has one end in fluid communication to the discharge end 4B of the fluid pump 4. Intake flow line 11 has a first end attached to the intake end 4A of fluid pump 4 and a second end in said reservoir 1 for delivering acid solution 3 to said membrane system 15.

For purposes of the present invention, the term acid tank/reservoir is defined as any size, nonreactive container for the storage of acid used in the present invention.

As shown in FIGS. 2 and 10, the acid solution 3 not only is a reactant making the conversion of $NH_3$ to $NH_4$ solid salts but also acts as a sweep, via the mechanical action of fluid pump 4, moving the salts to reservoir 1. These salts then can be used a fertilizer. Acids that can be used in the method of the invention include organic acids such as citric, oxalic, lactic, etc., mineral acids such as sulfuric, hydrochloric, nitric, phosphoric, for example, or a mixture of both mineral and organic acids or their precursors, such as sodium bisulfate, sulfur, corn silage, molasses, and carbohydrates or mixtures thereof etc. Approximately 1 Normal acid solutions are preferred.

Gaseous nitrogen producing can be treated by the addition of chemicals which enhance the volatilization of $NH_3$ from the litter. An example is an alkali chemical that converts $NH_4$—N to $NH_3$ according to ammonium-ammonia reaction: $NH_4^+ \rightarrow NH_3\uparrow + H^+$. Using calcium hydroxide (i.e. lime) as an example, the following equation defines the reaction: $Ca(OH)_2 + 2NH_4^+ \rightarrow 2NH_3\uparrow + Ca^{2+} 2H_2O$. Any chemical which will increase the volatilization of $NH_3$ from the litter can be used in the practice of this invention, such as calcium hydroxide, magnesium hydroxide, calcium oxide, magnesium oxide (and mixtures thereof), dolomitic lime, sodium hydroxide, and potassium hydroxide. The amount of alkali to apply depends on the degree of ammonia removal desired (see FIG. 12). Using lime as an example, a typical amount of ~2% (w/v) used for the disinfection of the litter will be sufficient to volatilize at least 80% of the ammonia from poultry litter. Lower amounts of lime in the range of 0.1-0.5% (w/v) will volatilize approximately 5 to 60% of the ammonia in the poultry litter. A simple test measuring ammonium in the poultry litter in KCl extracts (Peters et al., Ammonium nitrogen, p. 25-29, In J. Peters, ed. Recommended Methods of Manure Analysis. University of Wisconsin Extension, Madison, Wis., 2003) can be used to determine the rate of lime application for optimum ammonia volatilization. In this test, lime is applied at 3 to 5 rates between 0 and 2% (w/v), and the difference in KCL-extractable ammonium from the litter before and after lime application is taken as N loss.

The following examples are intended only to further illustrate the invention and are not intended to limit the scope of the invention which is defined by the claims. Poultry litter is used as a model to exemplify the system of the present invention. The system can be used for any enclosed space where $NH_3$ is produced and accumulated.

Example 1

This example includes four experiments for the process configuration wherein an acid solution is contained in an acid tank and was continuously recirculated into a chamber containing poultry litter (See FIG. 2). Once inside the chamber, the acid was contained inside a microporous, hydrophobic gas-permeable, tubular membrane 8 allowing for the passage of $NH_3$ gas emitted by the litter and subsequent recovery and concentration of the N as an ammonium salt.

Figure 3:
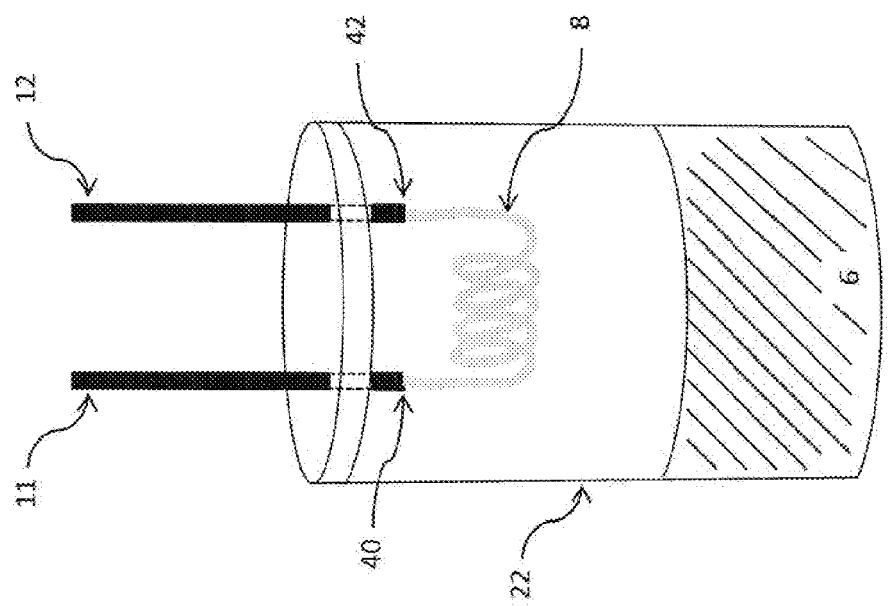
FIG. 3 is a drawing of a chamber used to determine the feasibility of using ePTFE gas-permeable membrane system to capture and recover $NH_3$ from poultry litter having gas permeable membrane 8, pump intake flow line 11 and pump discharge flow line 12, a membrane assembly entry opening 40 and a membrane assembly exit opening 42, and further showing enclosure/chamber 22, and $NH_3$, emitting source 6.

FIG. 3 shows a 2-L, polyethylene terephthalate (PET) plastic, wide-mouth jar 18 cm (h)×12 cm (dia) with a threaded polyethylene lid (Cole-Palmer, Vernon Hills, Ill., USA). There were a total of five ports in the lid of the chamber, two for acid inflow-outflow, one for venting air, through tubing with glass wool, to ensure ambient pressure and aerobic conditions inside the chamber, and the remaining ports, allowed headspace air sampling (only the inflow-outflow ports are depicted). Tygon tubing (approximately 4.75 mm I.D., 6.35 mm O.D., 0.8 mm wall thickness) was used for the inflow and outflow lines outside of the chamber. The chamber contained approximately 300 grams of poultry litter with a height inside the chamber of about 5 cm. The acid tank (FIG. 2) consisted of a 500 ml glass flask containing approximately 300 ml 1 N $H_2SO_4$. A peristaltic Manostat pump (Cole-Parmer, Vernon Hills, Ill., USA) was used to continuously pump the acid through the tubular membranes inside the chamber and back into the acid tank using flow rates of approximately 70-80 ml $day^{-1}$. The flow rate was selected from previous laboratory experiments that indicated that low (approximately 70-80 mL per day) or high (approximately 240-320 mL per day) flow rates of the acidic solution through the membrane system did not significantly affect $NH_3$ recovery (data not shown). Therefore, the lower flow rate was used to prolong the life of the pump tubing.

Figure 4:
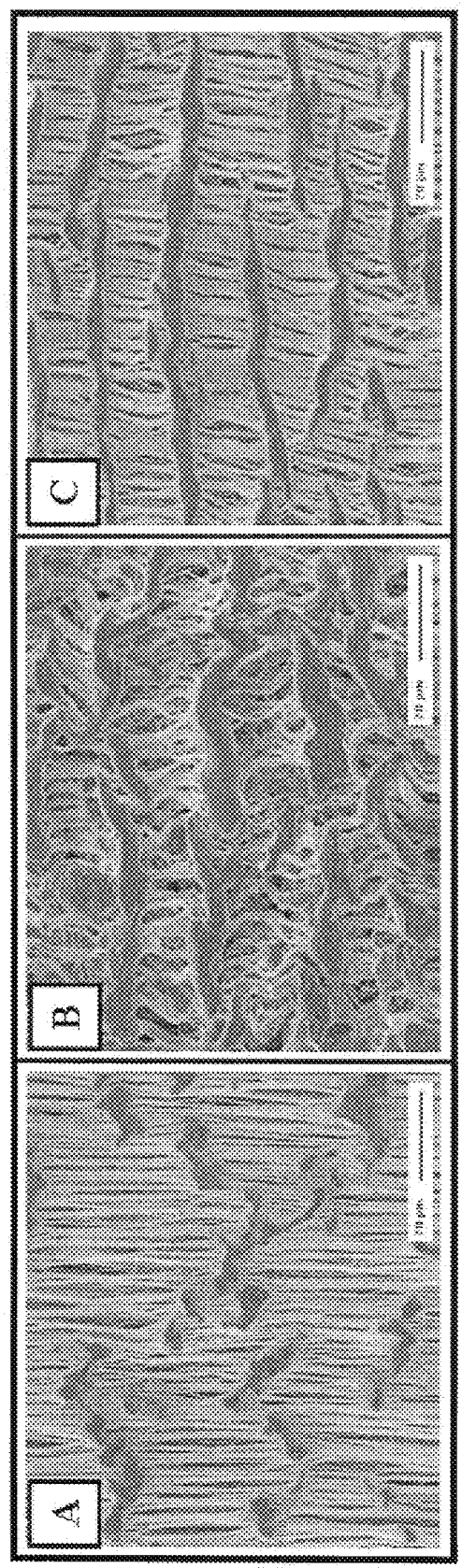
FIGS. 4(A-C) are scanning electron micrograph images for three different ePTFE tubular membranes showing different pore structures. All images are taken at 1000× magnification, and the scale bar is equivalent to approximately 20 µm in length. All three tubular membranes were used for the first/ experiment, while only ePTFE Type B (FIG. 4B) was used for subsequent experiments.

Expanded polytetrafluoroethylene (ePTFE)(Phillips Scientific Inc., Rock Hill, S.C.) was used in the interior of the chamber for $NH_3$ capture. The length of the tubing used in all experiments was approximately 66 cm. Characteristics of the ePTFE tubing and scanning electron micrographs for each of the three types of ePTFE tubing used in these studies are shown in Table 1 and FIG. 4, respectively.

TABLE 1

Physical characteristics of the different ePTFE tubular membranes used.

| Type | Inner Diameter (mm) | Wall Thickness (mm) | Bubble Point (kPa) |
|---|---|---|---|
| A | 4.00 | 0.25 | 34.5 |
| B | 5.25 | 1.00 | 241.3 |
| C | 8.75 | 0.75 | 206.8 |

Four experiments were performed to test the feasibility of using ePTFE tubular membranes in conjunction with an acidic solution to capture and recover $NH_3$. The first experiment determined the general application using three ePTFE membranes with different physical characteristics. The second experiment determined if $NH_3$ recovery could be enhanced with different placements of the membranes with respect to the litter surface. The third experiment determined the maximum capture capacity of the membranes by addition of excess urea to the poultry litter. The fourth experiment evaluated if the release of $NH_3$ from the litter could be recovered quickly through the use of hydrated lime treatments in combination with the use of membrane technology.

In all experiments, approximately 300 mL of 1 N $H_2SO_4$ was circulated at a flow rate of approximately 70-80 mL per day. Duplicate experiments were run for a total of 21 days. Add solution was sampled daily and headspace air (approximately 15-20 volumes) was sampled weekly. The pH of the acidic solution was monitored using pHydrion Insta-Chek 0-13 litmus paper (Micro Essential Laboratory, Brooklyn, N.Y.). For the air sampling, headspace air was evacuated from the chamber and the $NH_3$ was trapped in 1N $H_2SO_4$ via glass impingers according to Poach et al. (Journal of Environmental Quality, Volume 33, 844-851, 2004). After headspace evacuation, lids were removed, the litter was mixed using gloves, and a representative grab sample (about 12-15 grams) was taken prior to resealing the lid. Liquid samples were capped and stored at about 4 degrees G and litter samples were stored at about −20 degrees C. until analysis. Duplicate control chambers were set up containing lifter but no ePTFE tubing and sampled weekly to determine headspace $NH_3$ and litter characteristics without an $NH_3$ removal system. In addition, a 500-mL Erlenmeyer flask was set up as an acid tank control (not connected to any chamber) that was sampled at the same time as the other acid solution samples.

The bedding material that constituted the base of the broiler litter in all experiments was wood chips. Broiler litter used for the experiments was collected from a 25,000 bird broiler house in Lee County, S.C. At the time of sampling, the house was empty and between the second and third flock (five flocks per year). Two large composite litter samples were taken in two transects along the center section of the house (between water lines), and placed in 160-L containers. The containers were sealed and transported to the laboratory. Approximately 15 gram portion of the litter was passed through a 5.8 mm sieve and placed in cold storage (about −65 degrees C.) prior to laboratory experiments. The properties of the litter can be seen in Table 2 below. The starting weight of poultry litter was approximately 200 grams for each chamber, and all experiments were performed at ambient pressure and temperature room conditions.

TABLE 2

Poultry Litter properties

| Parameter | Unit | Value[a] |
|---|---|---|
| Moisture Content[b] | % | 19.7 |
| Volatile Solids[c] | % | 78.6 |
| pH | | 9.06 |
| Total N[d] | g kg$^{-1}$ | 26.3 |
| $NH_4$—N[d] | g kg$^{-1}$ | 13.7 |
| Total C[d] | g kg$^{-1}$ | 352 |

[a]Mean for triplicate litter samples (n = 3)
[b]Percent of total mass as measured after drying for 24 hours at 105° C.
[c]Percent of Total Solids, as measured after ashing at 550° C. for 30 mins.
[d]Dry weight basis All liquid samples were analyzed for $NH_4$—N according to Standard Method 4500-$NH_3$ G (APHA, 1998). Total Kjeldahl N (TKN) in solid samples was determined in digestion extracts using $H_2SO_4$ (Gallaher et al., Soil Science Society of American, Volume 4, 887-8891976). The $NH_4$—N and NO$_3$—N were extracted from the litter using a 60:1 2M KCl: litter mixture that was shaken (about 200 rpm) for about 30 minutes followed by gravity filtration through Whatman filter paper, size 42 (Whatman International Ltd., Maidstone, England) (Peters et al., Ammonium Nitrogen, P. 25-29, In. J. Peters (ed.) Recommended Methods of Manure Analysis. University of Wisconsin Extension, Madison, Wis., 2003). All NH$_4$—N, NO$_3$—N, and TKN analyses in solid samples were determined by colorimetry using the AutoAnalyzer II (Technicon, 1977; Technicon Instruments Corp., Tarrytown, N.Y.). Elemental analysis for total C and N was done by dry combustion (Leco Corp., St. Joseph, Mich.). All litter analyses were reported on a dry-weight basis. Moisture content of the poultry litter was determined by oven drying/the litter at about 105 degrees C. to constant weight. The dried sample was ignited in a muffle furnace at about 550 degrees C. for about 30 minutes to determine volatile solids (VS). Litter pH was measured electronically using a combination pH electrode at a 5:1 deionized water:litter ratio. Data were statistically analyzed by means and standard errors (proc MEANS), linear regression (proc REG), and analysis of variance (proc ANOVA), and least significant difference at a 0.05 probability level (LSD$_{0.05}$) for multiple comparisons among means with SAS version 9.2 (SAS, 2008).

Experiment 1

Figure 5:
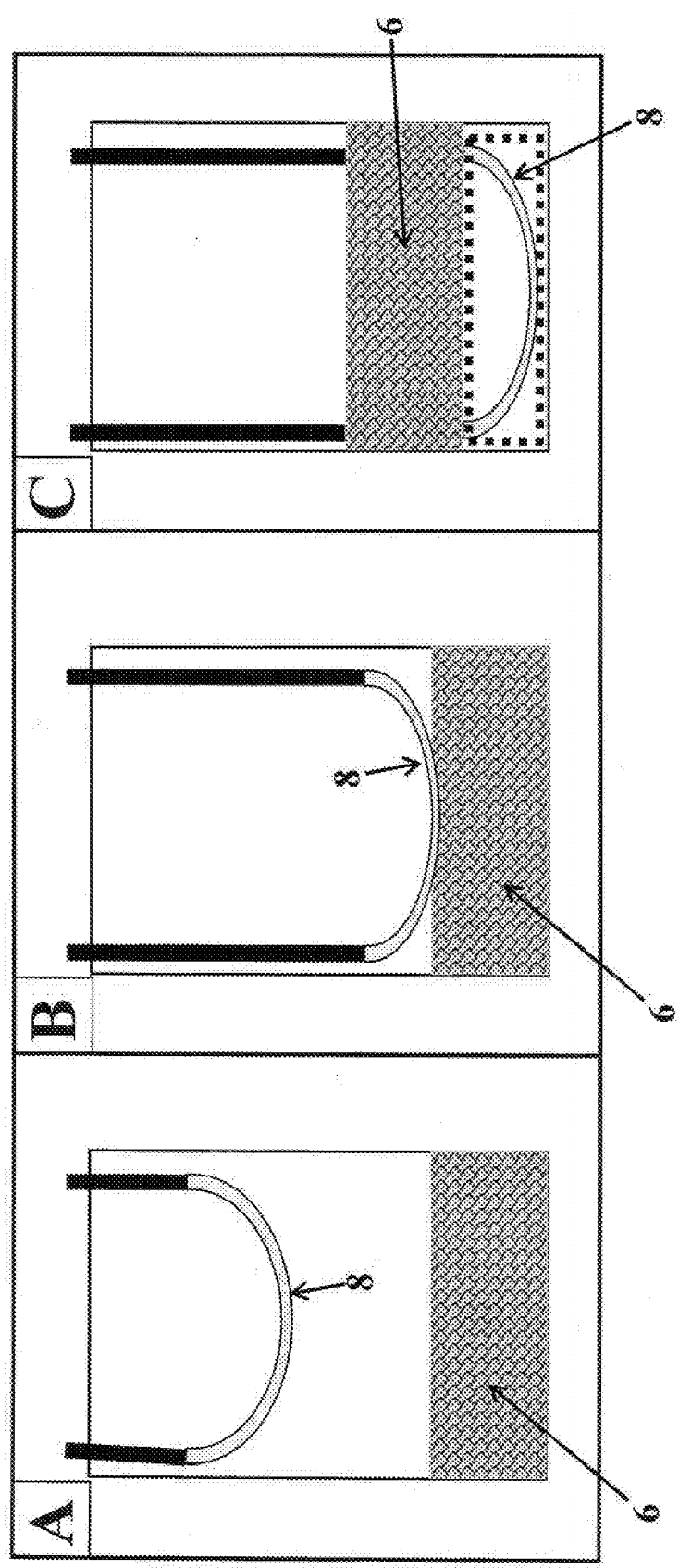
FIGS. 5 A-C are drawings showing positioning of the ePTFE tubular membranes 8 with respect to the emitting source 6 (poultry litter) surface in the Above (FIG. 5A), On (FIG. 5B), and Under (FIG. 5C) treatments. The black tubing represents the impermeable Tygon® tubing and the light tubing represents the gas-permeable ePTFE tubing. The dashed box surrounding the ePTFE in FIG. 5C represents the nylon mesh pocket that supported the ePTFE tubing under the litter.

The first experiment was designed to determine the general feasibility of using ePTFE tubular membranes on the recovery of NH$_3$ released from poultry litter. Three different ePTFE tubings were tested (Table 1 and FIG. 4), and identified as A, B, or C; distinguished by the following properties. Tubing A possessed an inner diameter of 4.00 mm, a wall thickness of 0.25 mm, and a bubble point of 34.5 kPa. Tubing B possessed an inner diameter of 5.25 mm, a wall thickness of 1.00 mm, and a bubble point of 241.3 kPa. Tubing C possessed an inner diameter of 8.75 mm, a wall thickness of 0.75 mm, and a bubble point of 206.3 kPa. The membrane tubing inside the chamber had the same length (approximately 66 cm) but varied in terms of wall thickness, pore size, and bubble points. Placement of the ePTFE tubing was approximately 5 cm above the litter surface (shown in FIG. 5A).

Figure 6:
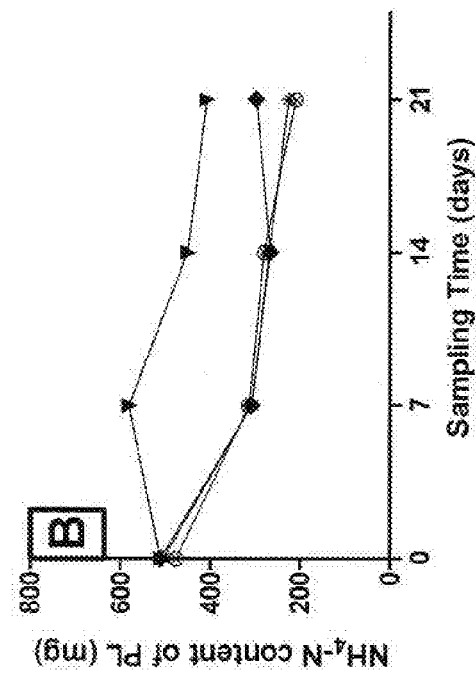
FIG. 6A is a graph which shows the mass of $NH_3$ recovered in the acidic solution and FIG. 6B is a graph which shows $NH_4$—N remaining in the poultry litter (PL) from chambers possessing three different types of ePTFE tubular membranes. The controls (▼) were run for both the acidic solution (A; acid without poultry Utter) and poultry litter (B; chamber without ePTFE $NH_3$ capture). All data points are the mean of duplicate chambers.
Figure 6:
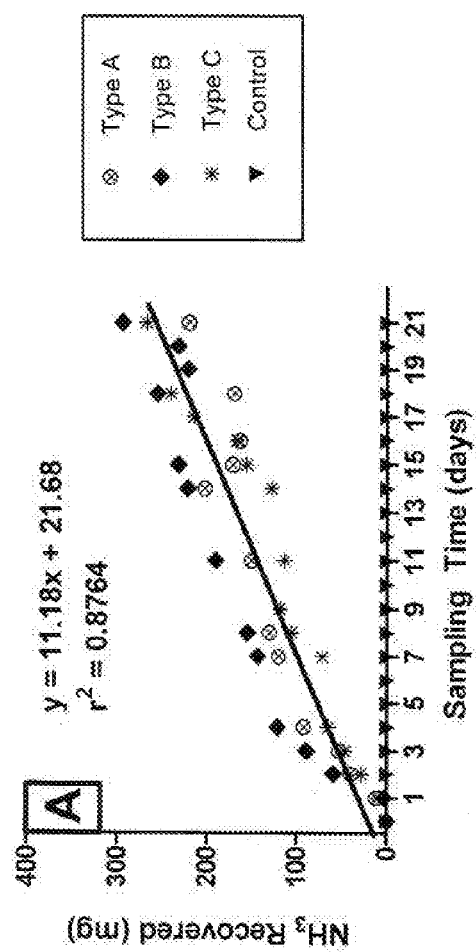

The membrane system recovered about 96% of the NH$_3$ lost from the litter during the 21 day evaluation (FIG. 6, Table 3). FIG. 6A shows a steady linear (y=11.18x+21.68, r$^2$=0.8764) increase in NH$_3$ accumulation in the acidic solution during the study as NH$_3$ was slowly released from the litter, as compared to the control where no NH$_3$ accumulated in the acidic solution. The three evaluated membranes performed similarly, with no significant difference in the total mass of NH$_4$—N accumulated in the acidic solution by the end of the experiment (Table 3). On the average, the total NH$_3$ recovered in the acidic solution was approximately 267.0 mg, compared to approximately 278.4 mg lost from the litter during the same period, resulting in approximately 96% mass recovery. The NH$_3$ capture rate, on a surface area basis, was approximately 1.37, 1.29, and 0.70 g m$^{-2}$ d$^{-1}$ for types A, B, and C, respectively. As the NH$_3$ was being recovered from the air with the membranes, the NH$_4$—N contained in the litter decreased accordingly; on the other hand, the NH$_4$—N content in the control treatment changed little (approximately 20%) throughout the experiment (FIG. 6B). This suggests that the removal of the NH$_3$ from the chamber using membranes allowed for a change in equilibrium concentration of ammoniacal-N in the litter. The high removal efficiencies obtained in this experiment showed that the use of NH$_3$ gas-permeable membranes for poultry litter application is feasible.

TABLE 3

Physical properties, mass balance and NH$_3$ capture rates of the three ePTFE tubular membranes after 21 days.

| TYPE | Properties | | Total NH$_4$—N Captured in Acidic Solution (mg)[b] | Total NH$_4$—N Lost from Litter (mg)[d] | NH$_4$—N Recovery % |
|---|---|---|---|---|---|
| | Surface Area (cm$^2$) | S/V (cm$^2$/cm$^{-3}$)[a] | | | |
| A | 83.2 | 10.0 | 240.2 (3.9)[c] | 267.2 (4.0) | 89.9 |
| B | 108.9 | 7.6 | 293 (5.2) | 287.8 (3.7) | 102.1 |
| C | 181.5 | 4.6 | 266.8 (5.4) | 280.1 (6.4) | 95.3 |
| Control | n/a | n/a | 0.0 | 102.1 (1.4) | 0.0 |
| LSD$_{0.05}$[e] | | | 54.02 | 69.33 | |

[a]Membrane surface to volume ratio.
[b]Total NH$_4$—N measured in the acid trap after 21 days incubation
[c]Mean (standard error of mean) for duplicate samples (n = 2).
[d]Total NH$_4$—N in the litter at the end of experiment calculated by subtracting NH$_4$—N content on day 21 from initial NH$_4$—N content on day 0.
[e]Least significant difference

Experiment 2

The second experiment was designed to determine if placement of the ePTFE tubing with respect to the litter surface had an effect on NH$_3$ recovery. Type B ePTFE tubing (Table 1) was used for this experiment. The tubing was placed inside the chamber in the following three positions (FIG. 5): (A) Above: approximately 5 cm above the litter surface; (B) On: laying directly on the litter surface, and (C) Under: below the litter and inside a pocket made of 300-μm nylon mesh (Krystal Klear Filtration, Winamac, Ind.) to support the tubing under the weight of the litter.

Figure 7:
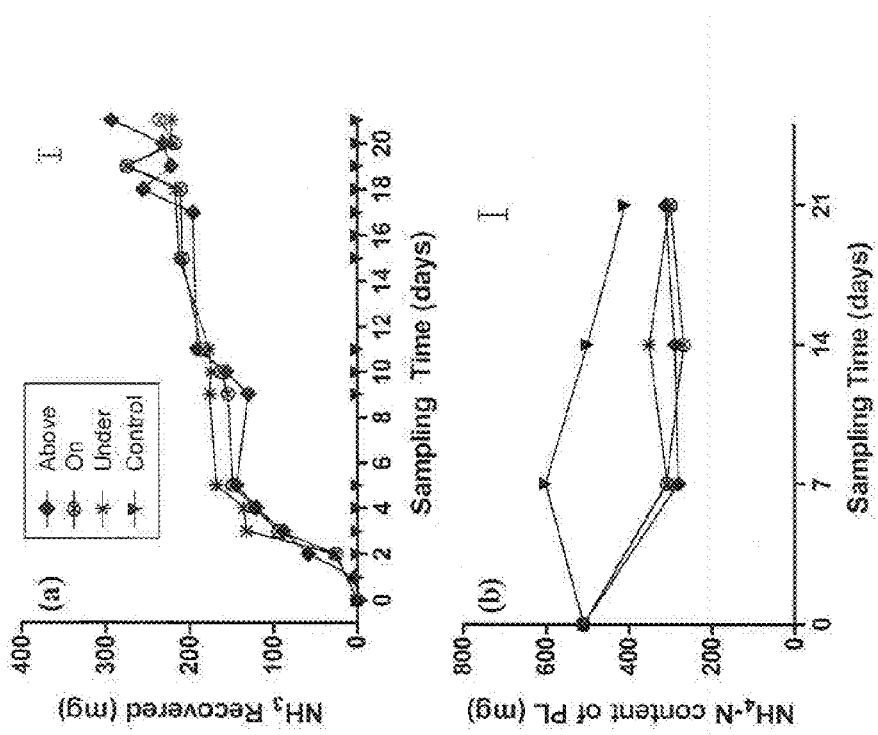
FIG. 7A is a graph showing the mass of $NH_3$ recovered in the acidic solution and FIG. 7B is a graph showing $NH_4$—N remaining in the poultry litter (PL) from chambers comparing the effect of membrane height from litter surface. The controls (▼) were run for both the acidic solution and poultry litter as described in FIG. 6. All points are the mean of duplicate chambers. The bar in the upper right corner of each graph represents the $LSD_{0.05}$ value for the $NH_3$ recovered in the acidic solution (approximately 27.992) and $NH_4$—N remaining in the litter (approximately 63.657).

The relative position of the tubular membranes (above, on, or under the litter) did not significantly affect the total mass of NH$_3$ recovery by the system (FIG. 7A, p=0.4776) nor the mass of the NH$_4$—N remaining in the litter after volatilization (FIG. 7B, p=0.7908). Therefore, the results of the three treatments were pooled together to perform a weekly mass balance of the NH$_4$—N in the chambers (Table 4). In terms of recovery efficiency, approximately 81.5% of the NH$_4$—N was recovered by the end of the third week. The NH$_3$ volatilized from the litter can move down and below the litter layer and be effectively recovered, as shown in the "under" treatment in FIG. 7A. This provides flexibility in future membrane treatment system design. For example, membrane manifolds may be placed below the bedding, or under caged production, thus minimizing exposure of birds to $NH_3$. Our results also show that aboveground placement of membrane manifolds is equally effective at recovering $NH_3$ from the litter, and these manifolds could be placed in grids near the surface or along waterer/feeder: lines, or even placed on the building walls.

TABLE 4

Weekly mass balance and percent recovery of $NH_3$ from pooled poultry litter samples from the three chambers with ePTFE tubular membranes at varying heights with respect to litter surface

| Sampling Time (days) | $NH_4$—N Content of Litter (mg kg$^{-1}$) | $NH_4$—N Mass Loss from Litter (mg)[b] | $NH_4$—N Mass Recovered in Acid Trap (mg) | $NH_4$—N Recovery (%) |
|---|---|---|---|---|
| 0 | 1369.2 (9.2)[a] | 0 | 0 | 0 |
| 7 | 758.3 (8.2) | 211.4 (4.1) | 172.5 (3.3) | 81.5 |
| 14 | 766.7 (9.9) | 208.4 (6.1) | 199.7 (3.7) | 95.8 |
| 21 | 791.7 (7.2) | 207.3 (4.0) | 230.0 (3.6) | 110.9 |

[a]Mean (standard error of the mean) of duplicate 2M KCl extractions of litter from the three treatments in experiment 2 (n = 3)
[b]Calculated by subtracting mass of $NH_4$—N at that sampling time from initial mass of $NH_4$—N in the litter Current $NH_3$ abatement technologies used in livestock houses rely on the ventilation systems and N treatment of the exhaust air after leaving the house (Melse and Ogink, Transactions of the ASAE, Volume 48(6), 2302-2313, 2005; Ndegwa et al., Biosystems Engineering, Volume 100, 453-469, 2008), but recent research has shown that $NH_3$ concentrations close to the litter surface (<20 cm), where the birds are exposed, can be up to one order of magnitude higher than in the bulk house air (Lahav et al., 2008, supra). A significant departure is the concept of Lahav et al., 2008 of removing $NH_3$ using manifolds that extract only the air close to the litter independent of the house ventilation system. The present invention, using a membrane system, follows the same concept, in that the $NH_3$ can be recovered near the litter with potential benefits to bird health and improved productivity, with the additional advantage that $NH_3$ is passively removed.

Experiment 3

The third experiment tested the capacity of the membranes to trap $NH_3$ by biologically enhancing the release of $NH_3$. To achieve this; organic nitrogen (approximately 10 grams of urea containing approximately 4.6 grams of nitrogen) was added to a chamber containing litter at the beginning of the experiment, resulting in a urea concentration of approximately 5% (w/w). This accounts for about twice the normal input of nitrogen for an entire grow-out, in an average house (Nabor and Bermudez, Poultry manure management and utilization problems and opportunities. Columbus, Ohio: Ohio State University, 1990). The added urea acted as a substrate to microbiologically enhance $NH_3$ production and volatilization from the litter. For comparison, a chamber with litter and 0% urea addition was used as a control treatment.

Excess urea (approximately 5% total mass) was added to the litter to determine how increased N input affected the $NH_4$—N mass potentially recovered by the ePTFE system. The amount of urea added was equal to approximately twice the N input of an average broiler over a typical grow-out period (about 42-56 days), assuming approximately 930 cm$^2$ (1 ft$^2$) of litter surface area is occupied per broiler. The above calculations assume that, on a dry weight basis, an average broiler produces approximately 37.5 g of manure daily, of which approximately 0.75 g (approximately 2% of total mass) is in a nitrogenous form (Naber and Bermudez, 1990). Initially, the total N content of the litter in the approximately 5% urea treatment chamber was approximately 16.39±0.86 g, with the urea accounting for approximately 42.8% (approximately 7.02 g) of the total N. For comparison, the litter from the non-amended (0%) treatment litter contained approximately 7.33±0.31 g of total N.

Figure 8:
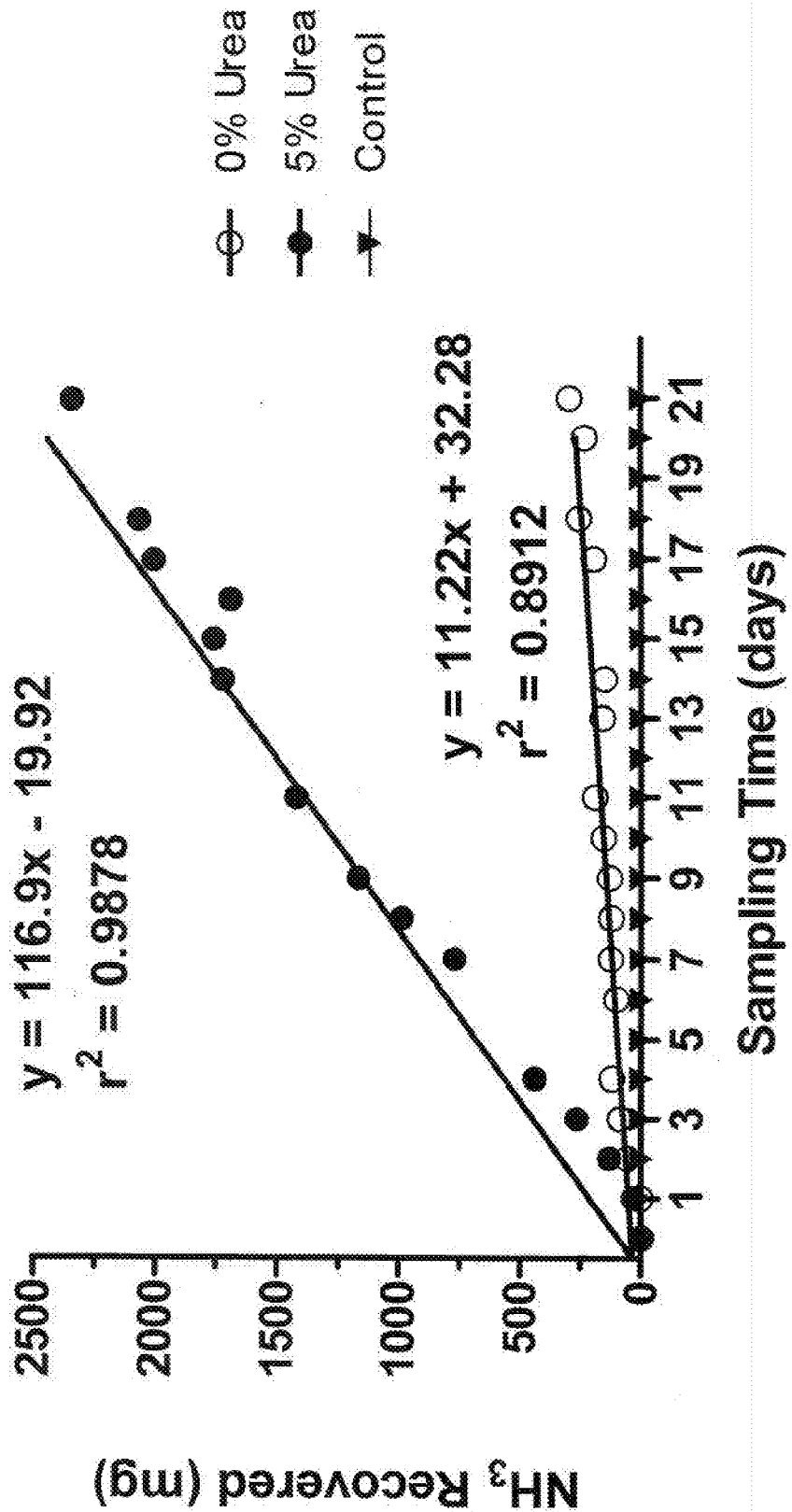
FIG. 8 is a graph showing the mass of $NH_3$ in the acidic solution from chambers amended with (approximately 5% w/w) or without urea as a nitrogen source to simulate the nitrogen input to the litter in a poultry house. A control (▼)

The addition of urea to the litter increased the recovery of $NH_3$ (approximately 2287.4±9.2 mg) as compared to the non-amended litter (approximately 293.9±26.6 mg). The corresponding rate of daily $NH_3$ capture per unit ePTFE surface area was approximately 10.5 g m$^{-2}$ d$^{-1}$ for the enhanced urea treatment and approximately 1.3 g m$^{-2}$ d$^{-1}$ for the non-amended litter (FIG. 8). The rate of $NH_3$ recovery in the approximately 5% urea treatment (approximately 116.9 mg d$^{-1}$) was significantly (p<0.0001) higher than in the 0% treatments (approximately 11.2 mg d$^{-1}$), according to regression analyses. These results indicate that the ePTFE system had higher capacity to recover $NH_3$ than in previous experiments (FIGS. 6 and 7; Tables 3 and 4), and that the limitation in those experiments was the amount of available $NH_3$. The concentration of $NH_4$—N in the acidic solution after 21 days was approximately 7859±96 mg/L, or 0.79%.

In addition to $NH_4$—N reduction in the litter, the membrane treatment also reduced $NH_3$ concentrations in the air. Measurements of $NH_3$ concentrations in the headspace air of the laboratory chamber after 7 days showed approximately 1.2±0.1 mg L$^{-1}$ $NH_3$ in the membrane system and approximately 17.5±0.2 mg L$^{-1}$ $NH_3$ in the control chamber without membrane. This represents about a 93% reduction in the headspace $NH_3$ concentrations in the membrane system.

The pH of the acidic solution in the 0% urea treatment was unchanged at day 21 compared to the beginning of the experiment, while the pH of the acidic solution from the approximately 5% urea treatment increased by about 2 pH units (from 0 to 2). This increase in pH indicates about a 99% reduction in the available protons (Lahav et al., Water Air Soil Pollution, Volume 191, 183-197, 2008) in the approximately 5% urea treatment after about 21 days as compared to the initial acidic solution and that the acidic solution would have needed to be recharged to recover additional $NH_3$. Therefore, it is important to keep up with the continuous supply of protons in this type of system so that the acidity is not limiting effective $NH_3$ recovery. Fortunately, we can use the pH of the acidic solution as an indication of acid recharge needs.

Experiment 4

The fourth experiment determined if $NH_3$ could be recovered quickly from the litter through the use of chemical treatment in combination with the use of membrane technology. To achieve this, amendments were added to the litter to chemically enhance $NH_3$ production and volatilization through the addition of hydrated lime, $Ca(OH)_2$ at four application rates of approximately 0%, 0.4%, 2%, and 4% w/v. Hydrated lime was mixed with the litter by vigorous shaking in a plastic bag and immediately placed in the chamber. Hydrated lime raised the pH of the litter (≥ to 10 units) to convert available non-volatile $NH_4$—N into volatile $NH_3$—N. Hydrated lime has been historically used for disinfection and $NH_3$ management of poultry litter (Shah et al., 2006, supra; Yushok and Bear, Poultry manure: Its preservation, deodorization, and disinfection. New Brunswick: N.J. Agricultural Experiment Station, 1948).

Figure 9:
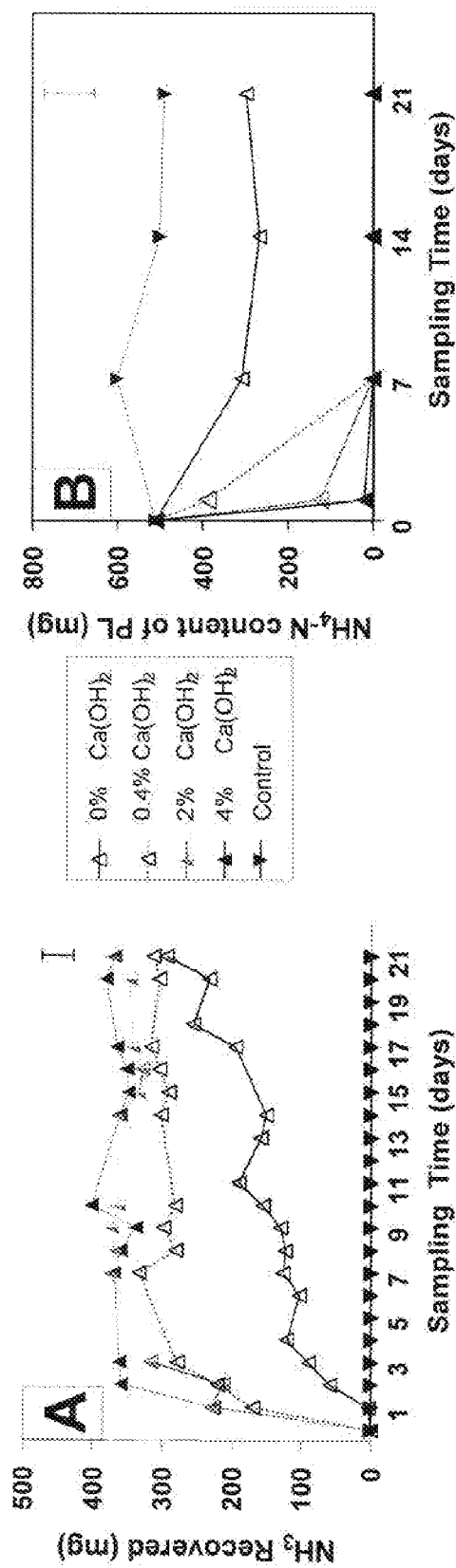

Hydrated lime [$Ca(OH)_2$] was applied to the litter at three rates of approximately 0.4%, 2%, and 4% w/v to increase the pH of the litter to rapidly transform $NH_4$—N into $NH_3$ gas and evaluate treatment time reduction compared to a control treatment (0% $Ca(OH)_2$ addition) (FIG. 9, Table 5). The addition ics to dimension the size of the membrane system because $NH_3$ release may be substantially different with natural or chemically enhanced systems.

TABLE 5

Mass balance, percent $NH_3$ recovery, and headspace $NH_3$ concentrations from poultry litter seven days after addition of three different hydrated lime rates

| Percent Hydrated Lime (w/v)[a] | $NH_4$—N Mass Loss from Litter (mg)[b] | $NH_3$ Mass Recovered in Acid Trap (mg) | $NH_3$ Recovery (%) | $NH_3$ Headspace Concentration without ePTFE (mg $L^{-1}$) | $NH_3$ Headspace Concentration with ePTFE (mg $L^{-1}$) |
|---|---|---|---|---|---|
| 0 | 202.0 (1.0)[c] | 146.3 (2.2) | 72.4 | 8.8 (0.1) | 0.2 (0.08) |
| 0.4 | 511.0 (4.7) | 333.0 (5.5) | 67.7 | 34.0 (1.4) | 0.0 (0.0) |
| 2 | 511.0 (4.7) | 376.3 (4.9) | 73.6 | 17.8 (1.4) | 0.0 (0.0) |
| 4 | 511.0 (4.7) | 389.4 (2.1) | 76.2 | 14.6 (1.6) | 0.0 (0.0) |
| $LSD_{0.05}$[d] | 14.55 | 63.93 | | 7.24 | 0.02 |

[a]Percent total mass of litter at the beginning of the experiment
[b]Calculated by subtracting mass of $NH_4$—N at day 7 from initial mass of $NH_4$—N in the litter
[c]Mean (standard error of the mean) of duplicate 2M KCl extractions of litter
[d]Least significant difference.

of approximately 0.4%, 2%, and 4% $Ca(OH)_2$ instantaneously increased the pH of the litter (approximately 10.23±0.10, 12.69±01, and 12.81±0.10, respectively) as compared to the litter without $Ca(OH)_2$ addition (approximately 8.96±0.02). As a consequence, the $NH_4$—N content of the litter decreased quickly within one day of chemical addition, from approximately 511.0±4.7 mg to approximately 388.9±5.3, approximately 124.4±5.9, and approximately 21.3±3.5 mg in the approximately 0.4%, 2%, and 4% $Ca(OH)_2$ treatments, respectively (FIG. 9B). Corresponding $NH_4$—N remaining in the litter after one day was approximately 76.1%, approximately 24.3%, and approximately 4.2%. After seven days, the $NH_4$—N content in the litter of all three chemically amended treatments was zero, indicating complete volatilization. In contrast, the $NH_4$—N content remaining in the control and 0% treatment was approximately 602.0±1.3 and approximately 202.0±1.0 mg, respectively (FIG. 9B), consistent with results obtained from the first and second experiments.

The increased $NH_3$ volatilization due to chemical addition significantly affected $NH_3$ recovery by the membrane system (FIG. 9A). Treatment time was reduced from about 21 days to less than about seven days. Ammonia was actively captured until days 7, 3, and 2 for the approximately 0.4%, 2%, and 4% treatments, respectively, at which point the recovered $NH_3$ reached a maximum and no significant additional $NH_3$ was captured in the acidic solution (FIG. 9A). In contrast, the treatment without hydrated lime addition slowly accumulated $NH_3$ in the acidic solution throughout the entire 21-day experiment. In terms of surface area of the membrane, the rates of $NH_3$ recovery were approximately 1.29, 4.94, 9.67, and 16.52 g $m^{-2}$ $d^{-1}$ for the approximately 0%, 0.4%, 2%, and 4% respectively. Therefore, the speed of $NH_3$ recovery by the membranes can be enhanced by increasing the pH of the litter, and commercially available hydrated lime is an effective chemical for this purpose.

The rapid flush of $NH_3$ by chemical addition exceeded the capacity of the membrane used in the bench-scale chamber, resulting in lower $NH_3$ recoveries after seven days between approximately 68%-76% (Table 5). For example, the membrane capacity in the approximately 4% w/v lime treatments in the first two days was approximately 180 mg $d^{-1}$ (FIG. 9A), which is lower than the approximately 490 mg of $NH_3$ released the first day after chemical addition (FIG. 9B). Therefore, it is important to consider the $NH_3$ release dynamics to dimension the size of the membrane system because $NH_3$ release may be substantially different with natural or chemically enhanced systems.

The use of a membrane system resulted in consistent decreases in headspace $NH_3$ concentrations for all four treatments as compared to the controls without membranes (Table 5, Columns 5, 6). $NH_3$ concentrations in the air were significantly (p<0.0001) reduced from approximately 8.8-34.0 mg $L^{-1}$ to approximately 0.2-0.0 mg $L^{-1}$ (approximately 97.7%-100% reduction).

An additional benefit of the use of hydrated lime is the disinfection of the poultry house. Lime has been shown to effectively destroy or inactivate bacterial and viral pathogens in poultry production facilities, including *Salmonella enteritidis* (Bennett et al., Effect of lime on *Salmonella enteritidis* survival in vitro. Journal of Applied Poultry Research 12:65-68, 2003) and H5N1 virus (causative agent of Avian Influenza; De Benedistis et al., Zoonoses Public Health 54:51-68, 2007). Therefore, producers choosing to disinfect their houses using lime could benefit from this membrane system by recovering the $NH_3$ rapidly released from the litter upon lime application.

Example 2

Flat, microporous, hydrophobic, gas-permeable membranes 8 (FIG. 10) are illustrated in this example for recovery of ammonia ($NH_3$) volatilized from poultry litter. A bench-scale prototype was used which comprised a plastic trough covered by a flat membrane of approximately 0.028 $m^2$ surface area, poultry litter (approximately 1 kg), and an acid solution (approximately 1 liter) within an enclosure (FIG. 10). This plastic trough covered with flat microporous, membrane (FIG. 15) consisted of a U-shaped PVC trough that measured about 11 cm width (top), 8 cm interior depth, and 29 cm length (Model No. 400, NDS, Inc.). The depth of the acid solution 3 flowing inside was about 2.5 cm and the depth of the membrane air space 16 between the surface of the acid and the insider of the membrane was about 4 cm. The flat gas-permeable membrane 8 was made of ePTFE with a thickness of 0.44 mm and a bubble point of 21 kPa (FL1001, Phillip Scientific, Inc.), and it was supported with a spunbond polypropylene fabric (0.229 mm thickness) that faced the acid. A PVC frame cover (Model No. 241-1, NDS, Inc.) with large openings (7×1 cm) that were uniformly spaced (0.5 cm) was used to fasten the membrane assembly to the trough. The acid solution was recirculated at a rate of approximately 10 L $d^{-1}$. Hydrated lime ($Ca(OH)_2$) was applied at different rates of approximately 0.1, 0.2, 0.5 and 2.0% w/v, to enhance ammonia volatilization by increasing litter pH. Each treatment was run in duplicate and a control treatment with no lime application (0% w/v) was also included. Changes in gaseous ammonia levels within the headspace of the enclosure and the levels of ammoniacal-N in the acid solution were monitored over a 4-day period. As a result of liming, gaseous $NH_3$ concentrations increased; rapidly in the headspace of the enclosures within approximately 6 hours for all $Ca(OH)_2$ treatments (FIG. 11), with higher $Ca(OH)_2$ application rates resulting in higher measured $NH_3$ concentrations in the air. As lime application rates increased, more $NH_3$ gas went in the air. However, in all lime treatments, the $NH_3$ gas decreased to a uniform level within 4 days with the membrane system (FIG. 11). As liming increases, more $NH_3$ is released into the air (FIG. 11) and consequently more N is recovered (FIG. 12). Therefore the amount of N removed by the membrane from the air is proportional to the concentration of ammonia in air. For example, after approximately one day 17.1, 184.3, 329.8, 609.6, and 742.3 mg $NH_3$—N were recovered in the approximately 0; 0.1, 0.2, 6:5, and 2.0% $Ca(OH)_2$ treatments, respectively. After two days, approximately 49.8, 284.3, 500.9, 927.2, and 1379.4 mg $NH_3$—N were recovered in the approximately 0, 0.1, 0.2, 0.5, and 2.0% $Ca(OH)_2$ treatments, respectively. After three days, approximately 71.0, 329.7, 528.5, 1084.5, and 1452.8 mg $NH_3$—N were recovered in the approximately 0, 0.1, 0.2, 0.5, and 2.0% $Ca(OH)_2$ treatments, respectively. After four days, approximately 106.8, 382.4, 598.2, 1266:2, and 1514.5 mg $NH_3$—N were recovered in the approximately 0, 0.1, 0.2, 0.5, and 2.0% $Ca(OH)_2$ treatments, respectively. Most of the recovery (>73%) occurred in the first two days (FIG. 12). By day 4, ≥87% of the ammoniacal-N lost from the litter was recovered in the acid solution for all treatments. These results demonstrated that flat, hydrophobic, gas-permeable membrane systems, can significantly reduce gaseous $NH_3$ contamination of air from poultry litter and recover the volatilized $NH_3$ in a liquid form.

Example 3

A field-scale prototype was used to further illustrate the ability of a microporous hydrophobic, gas-permeable, membrane system 15 using flat membranes to recover ammonia ($NH_3$) from $NH_3$ emitting source 6, i.e., poultry litter, m (FIGS. 13 and 14). Poultry litter 6 (approximately 32.5 kg) was placed inside an approximately 2.51 m³ enclosure 22 that contained a manifold system 17 with flat, hydrophobic, gas-permeable membrane 8 (FIGS. 13 and 14). The manifold system consisted of four troughs 7 (FIGS. 13 and 15) as described in Example 2 but with a length of approximately 1.3 m each connected in series with an acid flow pipe 18. The combined membrane surface area was approximately 0.4876 m². Approximately thirteen and a half L of an acid solution 3 was recirculated from the acid tank 1 to the membrane assembly 15 and back at a rate of approximately 27 L hr⁻¹. The experiment was done twice; once under normal conditions (no litter amendment), and the other with enhanced volatilization conditions using hydrated lime ($Ca(OH)_2$, approximately 2% w/v). The peak $NH_3$ concentration in the air (at approximately 24 hrs) was approximately 915 and >2000 ppmv in the normal and enhanced volatilization treatments, respectively. Results in Table 6 show that nearly all (>97.7%) of the $NH_3$ lost from the litter was recovered with the use of this invention. The liming increased volatilization of $NH_3$ from the litter (approximately 22.0% without lime and 100% with lime) and resulted in higher mass of N recovered (from approximately 29942 to approximately 48830 mg $NH_3$ in the approximately 0% and approximately 2% treatments, respectively). Even though the $NH_3$ was recovered efficiently in both situations, the average rate of recovery through the membrane (per unit surface area) was about 12% higher with the increased $NH_3$ availability due to liming (Table 6). We conclude that the performance efficiency of $NH_3$ removal with the gas-permeable membrane system is consistent across a Wide range of $NH_3$ volatilization conditions (normal or enhanced) in poultry manure.

TABLE 6

Recovery of ammonia using a field-scale flat membrane prototype system under normal and enhanced volatilization conditions[a,b]

| $Ca(OH)_2$ (w/v) | Initial $NH_3$ in Litter[c] | Final $NH_3$ in Litter[c] | $NH_3$ Lost from Litter[d,e] | $NH_3$ Recovered in the Acid Solution | $NH_3$ Recovery[f] | $NH_3$ Recovery Rate[g] |
|---|---|---|---|---|---|---|
| % | | | mg | | % | mg $NH_3$ m⁻² d⁻¹ |
| 0 | 139236 | 108590 | 30646 | 29942 | 97.7 | 7011 |
| 2 | 48427 | 0 | 48427 | 48830 | 100.8 | 7867 |

[a]32.5 kg litter in a 2.51 m³ enclosure
[b]Days of experiment: 0% = 8.76 days; 2% = 12.73 days
[c]Measured using 2M KCl extraction method and colorimetry using an autoanalyzer (Peters et al., Ammonium nitrogen, p. 25-29, In J. Peters, ed. Recommended Methods of Manure Analysis. University of Wisconsin extension, Madison, WI., 2003)
[d]Peak gaseous $NH_3$ concentration in air: 0% = 915 ppmv; 2% = >2000 ppmv
[e]$NH_3$ Lost from Litter = Initial Litter $NH_3$ − Final Litter $NH_3$
[f]$NH_3$ Recovery = ($NH_3$ Recovered in Acid/$NH_3$ Lost from Litter) * 100
[g]Based on 0.4876 m² of flat membrane surface area per prototype It will be clear to a person skilled in the art that the scope of the present invention is not limited to the examples discussed above, but that various changes and modifications thereof are possible without departing from the scope Index of the invention as defined in the appended claims.

INDEX OF THE ELEMENTS

1. Acid tank or reservoir
3. Acid Solution
4. Fluid Pump
4A. Intake End
4B. Discharge End
6. $NH_3$ Emitting Source
7. Trough covered with flat membrane
8. Hydrophobic gas-permeable membrane 8A. Outer Surface of Membrane
8B. Inner Surface of Membrane
9. Membrane Pores
10. Hollow Inferior of Tubular Membrane
11. Intake Flow Line
12. Discharge Flow Line
15. Membrane Assembly/System
16. Membrane Air Space between the Inner Surface of Membrane and Surface of the Acid Solution.
17. Membrane Manifold System
18. Acid flow Pipes
20. Ammonia Capture System
22. Chamber/Enclosure
26. Floor
40 Membrane Assembly Entry Opening
42. Membrane Assembly Exit Opening

What is claimed:

1. A system for reducing ammonia concentration within an enclosure comprising:
   (a) a gas permeable membrane placed inside an enclosure having a floor and containing an ammonia gas emitting source located on the floor of said enclosure wherein said permeable membrane allows for the diffusion of ammonia gas from the ammonia gas emitting source through the membrane,
   (b) a reservoir containing an acid supply in closed loop fluid communication with said membrane;
   (c) an acid for chemically changing the ammonia gas to ammonium salts in closed loop communication with said reservoir and said membrane;
   (d) a delivery system for delivering said acid from the reservoir to the gas permeable membrane and for carrying the salts from the membrane to the reservoir for storage.

2. The system according to claim 1 wherein said gas permeable membrane is selected from the group consisting of at least one tubular gas permeable membrane and at least flat gas permeable membrane stretched over a trough.

3. The system according to claim 2 wherein said gas permeable membrane is a tubular gas membrane.

4. The system according to claim 3 further comprising a pump having an intake end and discharge end and a first and a second hollow flow line having distal and proximal ends, wherein the first line is attached at one end to the discharge end of the pump and a second end is attached to a first opening of a tubular gas membrane; and the second line has a first end attached to a second opening of said tubular gas permeable membrane and a second end disposed above or in said reservoir for discharging ammonium salts to said reservoir.

5. The system according to claim 2 wherein said membrane is a flat gas permeable membrane stretched over a trough.

6. The system according to claim 5 further comprising a pump having an intake end and a discharge end, and at least a first and a second hollow flow line having distal and proximal ends, wherein the first line is attached at one end to the discharge end of the pump and a second end is attached to an membrane assembly entry opening of the gas permeable membrane trough having a flat gas permeable membrane; and the second line has a first end attached to an membrane assembly exit opening of the gas permeable membrane trough having a flat gas permeable membrane and a second end disposed above or in said reservoir for discharging ammonium salts to said reservoir.

7. The system according to claim 1 wherein said gas permeable membrane is suspended above the floor covered with said ammonia emitting source.

8. The system according to claim 1 wherein said gas permeable membrane is located beneath the floor covered with said ammonia emitting source.

9. The system according to claim 1 wherein said gas permeable membrane is located on a floor covered by said ammonia emitting source.

10. The system according to claim 1 wherein said acid is selected from the group consisting of organic acids, mineral acids, precursors of organic acids and mineral acids, and mixtures thereof.

11. The system according to claim 10 wherein said organic acid is selected from the group consisting of citric, oxalic, lactic, or mixtures thereof.

12. The system according to claim 10 wherein said mineral acid is selected from the group consisting of sulfuric, hydrochloric, nitric, phosphoric, and mixtures thereof.

13. The system according to claim 10 wherein said precursor of said acids are selected from the group consisting of sodium bisulfate, sulfur, corn silage, molasses, carbohydrates, and mixtures thereof.

* * * * *